United States Patent
Xian et al.

(10) Patent No.: US 9,096,504 B2
(45) Date of Patent: Aug. 4, 2015

(54) CONTROLLED CHEMICAL RELEASE OF HYDROGEN SULFIDE

(75) Inventors: Ming Xian, Pullman, WA (US); Yu Zhao, Pullman, WA (US)

(73) Assignee: Washington State University, Pullman, WA (US)

( * ) Notice: Subject to any disclaimer, the term of this patent is extended or adjusted under 35 U.S.C. 154(b) by 46 days.

(21) Appl. No.: 13/989,971

(22) PCT Filed: Dec. 1, 2011

(86) PCT No.: PCT/US2011/062820
§ 371 (c)(1),
(2), (4) Date: May 28, 2013

(87) PCT Pub. No.: WO2012/075242
PCT Pub. Date: Jun. 7, 2012

(65) Prior Publication Data
US 2013/0253051 A1    Sep. 26, 2013

Related U.S. Application Data

(60) Provisional application No. 61/418,760, filed on Dec. 1, 2010.

(51) Int. Cl.
| | | |
|---|---|---|
| A61K 31/21 | (2006.01) |
| C07C 381/00 | (2006.01) |
| A61K 31/095 | (2006.01) |
| A61K 31/165 | (2006.01) |
| A61K 31/166 | (2006.01) |
| C07C 327/00 | (2006.01) |

(52) U.S. Cl.
CPC ............ *C07C 381/00* (2013.01); *A61K 31/095* (2013.01); *A61K 31/165* (2013.01); *A61K 31/166* (2013.01); *C07C 327/00* (2013.01)

(58) Field of Classification Search
USPC .................. 514/506, 608; 564/102; 560/302
See application file for complete search history.

(56) References Cited

U.S. PATENT DOCUMENTS 7,799,782 B2 *    9/2010  Munson et al. ............ 514/234.5
2010/0273743 A1 * 10/2010  Moore et al. .................... 514/90

OTHER PUBLICATIONS

Benavides et al., "Hydrogen sulfide mediates the vascoactivity of garlic", Proc. Natl. Acad. Sci. USA, Nov. 13, 2007, pp. 17977-17982, vol. 104, No. 46.
Li et al., "Anti-inflammatory and gastrointestinal effects of a novel diclofenac derivative", Free Radic. Biol. Med., Mar. 1, 2007, pp. 706-719, vol. 42, No. 5.
Zhao et al., "Cysteine-activated hydrogen sulfide (H2S) donors", J. Am. Chem. Soci., Dec. 10, 2010, pp. 15-17, vol. 133, No. 1.

* cited by examiner

*Primary Examiner* — Rei-Tsang Shiao
(74) *Attorney, Agent, or Firm* — Whitham Curtis Christofferson & Cook, PC

(57) ABSTRACT

Agents of formula: where R1 and R2 vary independently and are acyl, sulfonyl, phosphoryl, alkyl, substituted alkyl, halogen, aryl, arylalkyl, substituted aryl, heteroaryl, alkenyl, substituted alkenyl, alkynyl, substituted alkynyl, cycloalkyl, heterocycle, or heteroatoms; and R3 is H or a member of a ring structure which includes R2, are provided; as are agents of formula: where R1, R2 and R3 vary independently and: R1=OH, OR', NHR', NR'R" (with R' R"=alkyl, aryl, heteroaryl, etc); R2=acyl, alkyl, aryl, sulfonyl, etc; R3=alkyl, aryl, substituted aryl, heteroaryl, etc; and R4 and R5 are (independently) H, methyl or alkyl, substituted alkyl, aryl, substituted aryl, etc. Methods of using the agents to treat e.g. cardiovascular disease, stroke, shock, injuries caused by hypoxia, male erectile dysfunction, and Alzheimer's are provided.

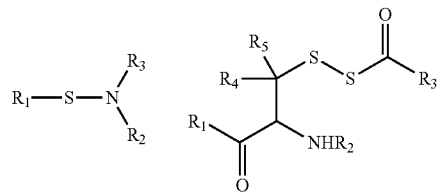

3 Claims, 2 Drawing Sheets

CONTROLLED CHEMICAL RELEASE OF HYDROGEN SULFIDE

CROSS-REFERENCE TO RELATED APPLICATIONS

This application is a Rule 371 national stage application based on PCT/US2011/62820 filed Dec. 1, 2011, and claims priority to U.S. Ser. No. 61/418,760 filed Dec. 1, 2010.

BACKGROUND OF THE INVENTION

1. Field of the Invention

The invention generally relates to agents and methods for releasing $H_2S$ in an aqueous environment. In particular, the invention provides agents of various formulations which release $H_2S$ in a controlled, predictable and sustained manner upon contact with an aqueous environment, such as the circulatory system of an animal, and which are thus suitable for in vivo delivery of $H_2S$.

2. Background of the Invention

Hydrogen sulfide ($H_2S$) is a noxious gas with the characteristic smell of rotten eggs. Recent studies recognized $H_2S$ as the third gaseous transmitter beside nitric oxide (NO) and carbon monoxide (CO) that influence various physiological processes. (Calvert 2010, Gadalla 2010, Szabo 2007, Lowicka 2007, Blackstone 2005) $H_2S$ has been shown to relax vascular smooth muscles, mediate neurotransmission, elicit hibernation, inhibit insulin signalling, regulate inflammation and blood vessel caliber. (Calvert 2010, Gadalla 2010, Szabo 2007, Lowicka 2007, Blackstone 2005) Endogenous formation of $H_2S$ is achieved by enzymes such as cystathionine-β-synthase (CBS) in the brain and cystathionine-γ-lyase (CSE) in liver, vascular and non-vascular smooth muscle. Although its exact chemical and biochemical modes of action are still not fully understood, levels of $H_2S$ in the brain and vasculature have unambiguously been associated with human health and disease. (Calvert 2010, Gadalla 2010, Szabo 2007, Lowicka 2007, Blackstone 2005)

To study the physiological and pathophysiological properties of $H_2S$, the direct use of $H_2S$ gas or NaHS in aqueous solutions are typical. However, the therapeutic potential of $H_2S$ gas seems to be limited due to difficulties in obtaining precisely controlled concentrations and possible toxic impact of $H_2S$ excess. NaHS, although widely used as a research tool, is a short-lasting donor which does not mimic the slow and continuous process of $H_2S$ generation in vivo. In addition, NaHS in aqueous solution can be rapidly oxidized by $O_2$. Modifications that are made between the time that a solution is prepared and the time that the biological effect is measured can dramatically affect results. Due to these limitations, $H_2S$-releasing agents (i.e. $H_2S$ donors) are considered useful tools in the study of $H_2S$. (Calvert 2010, Gadalla 2010, Szabo 2007, Lowicka 2007, Blackstone 2005, Caliendo 2010, Jacob 2008) However, currently available $H_2S$ donors are very limited. (Calvert 2010, Gadalla 2010, Szabo 2007, Lowicka 2007, Blackstone 2005, Caliendo 2010, Jacob 2008) Besides NaHS, only three types of $H_2S$ donors have been reported: 1) garlic-derived polysulfide compounds, such as diallyl trisulfide (DATS). $H_2S$ release from DATS was suggested to mediate the vasoactivity of garlic. (Benavides 2007) 2) GYY4137, a Lawesson's reagent derivative, is a synthetic $H_2S$ donor. This molecule decomposes spontaneously in aqueous buffers to release $H_2S$. (Li 2009, Li 2008) 3) A dithiolthione moiety as a $H_2S$ donor has been used to prepare $H_2S$—nonsteroidal anti-inflammatory drug hybrids like S-diclofenac. (Baskar 2008) In addition, biological thiols such as cysteine and glutathione can be $H_2S$ donors upon enzymatic or thermal treatment (Morra 1991). A limitation of these known donors is that $H_2S$ release is too fast to mimic biological $H_2S$ generation. Given the structural characters of these compounds, little can be done to modify their structures to control the release of $H_2S$. Therefore, developing new $H_2S$ donors with controllable $H_2S$ generation capability is critical for this field. Ideal $H_2S$ donors, from a therapeutic point of view and for applications in $H_2S$-related biological research, should release $H_2S$ slowly and in moderate amounts. (Caliendo 2010, Jacob 2008). There is a need for the development of chemical agents capable of controllably releasing $H_2S$ for use within biological systems.

SUMMARY OF THE INVENTION

Herein are disclosed agents and associated methods for the sustained chemical release of $H_2S$ in aqueous environments, such as in vivo (e.g. for therapeutic purposes) or in vitro (e.g. for research or other purposes). Upon exposure to an aqueous milieu, the agents break down slowly into products which include $H_2S$, and thus deliver the $H_2S$ steadily and at a predictable rate to the surrounding medium. The agents thus overcome the limitations of the prior art with respect to the delivery of $H_2S$ to a location of interest, e.g. the circulatory system of a subject, and successfully function as to mimic natural, biological delivery of $H_2S$. As such, the agents are used to treat diseases or conditions that can be cured or ameliorated by the delivery of $H_2S$ and/or by an increase in the concentration of $H_2S$ at a location or environment of interest. The agents may also be used for research purposes, as well as for the protection or preservation of biological material outside the body, e.g. to protect tissues and organs that are to be used for tissue/organ transplant. Industrial and/or manufacturing uses are also within the scope of the invention.

DETAILED DESCRIPTION

Figure 1:
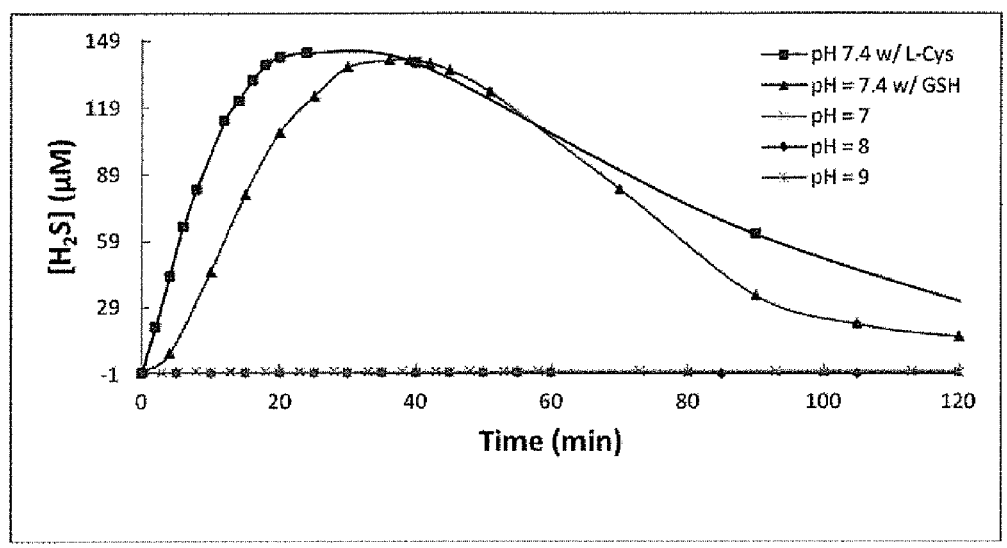
FIG. 1: $H_2S$ generation curve for compound 2.

The invention provides compounds which function as agents for the delivery of $H_2S$ to an aqueous environment of interest, e.g. the circulatory system of an animal, or to other systems where the slow, measured release of $H_2S$ is desirable.

In one embodiment, the agents of the invention are of the general formula provided by Formula 1:

Formula 1 in which R1 and R2 can be independently varied and comprise an acyl, sulfonyl, phosphoryl, alkyl, substituted alkyl, halogen, aryl, aralkyl, substituted aryl, heteroaryl, alkenyl, substituted alkenyl, alkynyl, substituted alkynyl, cycloalkyl, heterocycle, heteroatoms or any combination thereof; and wherein R3 is H or acyl, sulfonyl, phosphoryl, alkyl, substituted alkyl, halogen, aryl, aralkyl, substituted aryl, heteroaryl, alkenyl, substituted alkenyl, alkynyl, substituted alkynyl, cycloalkyl, heterocycle, heteroatoms or any combination thereof, or a member of a ring structure which includes R2. Exemplary ring structures include but are not limited to:

cycloalkyl rings (such as pyrrolindine, piperidine, quinoline, indoline, acridine), cycloacyl rings (such as piperidinone, pyrrolidinone, piperidinedione, pyrrolidinedione)

In embodiments of Formula 1 in which R3 is H, the general formula of the agent is as follows:

Formula 2

in which R1 and R2 can be independently varied and comprise an acyl, sulfonyl, phosphoryl, alkyl, substituted alkyl, halogen, aryl, aralkyl, substituted aryl, heteroaryl, alkenyl, substituted alkenyl, alkynyl, substituted alkynyl, cycloalkyl, heterocycle, heteroatoms or any combination thereof, as described above for Formula 1.

Without being bound by theory, it appears that compounds of Formula 2 may generally act to release hydrogen sulfide in accordance with Scheme 1:

Scheme 1

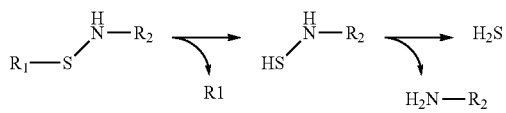

Hydrogen sulfide release from agents of Formula 2 follows a process whereby a first group chemically bound to the sulfur atom is released. The release of the first chemical group can be triggered by, for example, nucleophillic or electrophillic attack of an environmental constituent, a photochemical, thermal, or electrochemically induced breakage of the chemical bond between R1 and S. It is important to note that there may be multiple steps, or a cascade of chemical rearrangements that ultimately result in the breakage of the chemical bond that link R1 and S, moreover there may be subsequent degradation of R1 after its release from Formula 2. The product of the release of R1 is a quazi-stable SH-amide structure which, upon reduction via chemical, electrochemical, photochemical, or thermochemical means, results in the formation of a primary amine and hydrogen sulfide.

In other embodiments of Formula 1, R3 is a member of a ring structure which includes R2. In other words, both R2 and R3 are incorporated into a ring or cyclic structure. The ring structure may be, for example, cycloalkyl rings (such as pyrrolindine, piperidine, quinoline, indoline, acridine), cycloacyl rings (such as piperidinone, pyrrolidinone, piperidinedione, pyrrolidinedione).

Without being bound by theory, compounds in which both R2 and R3 are members of a ring or cyclic structure may generally act to release hydrogen sulfide in accordance with Scheme 2:

Scheme 2

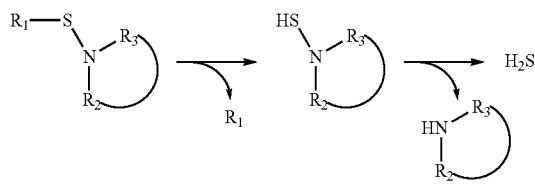

Hydrogen sulfide release from this type of agents follows a process whereby a first group chemically bound to the sulfur atom is released. The release of the first chemical group can be triggered by, for example, nucleophillic or electrophillic attack of an environmental constituent, or a photochemical, thermal, or electrochemically induced breakage of the chemical bond between R1 and S. It is important to note that there may be multiple steps, or a cascade of chemical rearrangements that ultimately result in the breakage of the chemical bond that links R1 and S. The product of the release of R1 is a quazi-stable SH-amine structure which, upon reduction via chemical, electrochemical, photochemical, or thermochemical means, results in the formation of an amine and hydrogen sulfide.

In yet another embodiments, agents and associated methods for the chemical release of $H_2S$ (hydrogen sulfide) from perthiol compounds as depicted in Formula 3 are disclosed:

Formula 3

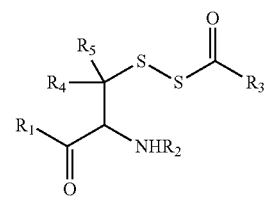

where R1, R2 and R3 may vary independently and: R1=OH, OR', NHR', NR'R" (with R' and R"=alkyl, aryl, heteroaryl, etc.); R2=acyl, alkyl, aryl, sulfonyl, etc.; R3=alkyl, aryl, substituted aryl, heteroaryl, etc.; and R4 and R5 are (independently) H, methyl or alkyl, substituted alkyl, aryl, substituted aryl, etc.

When R4 and R5 are both H, the compounds are referred to as cycteine based perthiols. A generic representation of these compounds is as depicted in Formula 4:

Formula 4

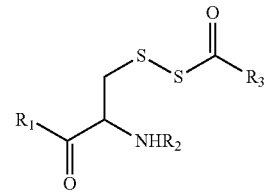

where R1, R2 and R3 are as described above for Formula 3.

When R4 and R5 are both $CH_3$, the compounds are referred to as penicillamine based perthiols. A generic representation of these compounds is as depicted in Formula 5:

Formula 5

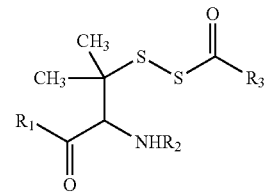

where R1, R2 and R3 are as described above for Formula 3.

DEFINITIONS

The following are definitions of terms that may be used in the present specification. The initial definition provided for a group or term herein applies to that group or term throughout the present specification individually or as part of another group, unless otherwise indicated.

The term "acyl" refers to or denotes a chemical group containing the monovalent group of atoms RCO—, where R is an organic group. Acyl groups contain at least one carboxylic-acid-derived chemical group, e.g. a chemical group derived from a carboxylic acid by removal of a hydroxyl group. In organic chemistry, the acyl group is usually derived from a carboxylic acid (IUPAC name: alkanoyl). Therefore, it has the formula RCO—, where R represents e.g. an alkyl group that is attached to the CO group with a single bond. Representative acyl groups include but are not limited to formyl, acetyl, propionyl, acrylyl, etc. Although the term is almost always applied to organic compounds, acyl groups can in principle be derived from other types of acids such as sulfonic acids, phosphonic acids. In the most common arrangement, acyl groups are attached to a larger molecular fragment, in which case the carbon and oxygen atoms are linked by a double bond.

The term "alkyl" refers to straight or branched chain unsubstituted hydrocarbon groups of 1 to 20 carbon atoms, preferably 1 to 7 carbon atoms. The expression "lower alkyl" refers to unsubstituted alkyl groups of 1 to 4 carbon atoms.

The term "substituted alkyl" refers to an alkyl group substituted by, for example, one to four substituents, such as, halo, hydroxy, alkoxy, oxo, alkanoyl, aryloxy, alkanoyloxy, amino, alkylamino, substituted alkylamino, cycloalkylamino, substituted cycloalkylamino, acylamino, substituted arylamino, aralkylamino, substituted aralkyamino, disubstituted amines in which the 2 amino substituents are selected from alkyl, aryl or aralkyl; alkanoylamino, aroylamino, aralkanoylamino, substituted alkanoylamino, substituted arylamino, substituted aralkanoylamino, thiol, alkylthio, arylthio, aralkylthio, alkylthiono, arylthiono, aralkylthiono, alkylsulfonyl, arylsulfonyl, aralkylsulfonyl, sulfonamido, e.g. $SO_2NH_2$, substituted sulfonamido, nitro, cyano, carboxy, carbamyl, e.g. $CONH_2$, substituted carbamyl e.g. CONHalkyl, CONHaryl, CONHaralkyl or cases where there are two substituents on the nitrogen selected from alkyl, aryl or aralkyl; alkoxycarbonyl, aryl, substituted aryl, guanidino, heterocyclyl, e.g., indolyl, imidazolyl, furyl, thienyl, thiazolyl, pyrrolidyl, pyridyl, pyrimidyl, pyrrolidinyl, piperidinyl, morpholinyl, piperazinyl, homopiperazinyl and the like, and substituted heterocyclyl. Where noted above where the substituent is further substituted it will be with alkyl, alkoxy, aryl or aralkyl.

The term "halogen" or "halo" refers to fluorine, chlorine, bromine and iodine.

The term "ring structure" refers to an organic cyclic compound i.e. an organic compound in which a series of atoms is connected to form a loop or ring. The term includes various cyclic compounds, which may be: saturated, unsaturated or aromatic; substituted or unsubstituted; hetero- or homo-cyclic; and may be mono- or polycyclic, as described herein.

As used herein hetero-structures are those in which not all atoms of the primary structure (e.g. a cycloalkyl ring) are carbon. Instead, one or more are a different atom, e.g. a 6-membered ring in which 5 of the ring atoms are C and one is N.

As used herein the term "substituted" refers to hydrocarbon compound (e.g. an alkyl, alkenyl, alkynyl, ring, etc. structure as described herein) in which an H bonded to a C is replaced or substituted by a different atom or groups of atoms e.g. a saturated 6-membered straight chain in which the 2 terminal C atoms are bonded to three H atoms, three of the four internal C atoms are bonded to 2H atoms, and one of the internal C atoms is bonded to H and also to a different atom or group of atoms (e.g. OH). In this case, the hydrocarbon chain is "substituted" by (with) OH.

The term "aryl" refers to monocyclic or bicyclic aromatic hydrocarbon groups having 6 to 12 carbon atoms in the ring portion, such as phenyl, naphthyl, biphenyl and diphenyl groups, each of which may be substituted.

The term "aralkyl" refers to an aryl or a substituted aryl group bonded directly through an alkyl group, such as benzyl.

The term "substituted aryl" refers to an aryl group substituted by, for example, one to four substituents such as alkyl, substituted alkyl, alkenyl, substituted alkenyl, alkynyl, substituted alkynyl, aryl, substituted aryl, aralkyl, halo, trifluoromethoxy, trifluoromethyl, hydroxy, alkoxy, alkanoyl, alkanoyloxy, aryloxy, aralkyloxy, amino, alkylamino, arylamino, aralkylamino, dialkylamino, alkanoylamino, thiol, alkylthio, ureido, nitro, cyano, carboxy, carboxyalkyl, carbamyl, alkoxycarbonyl, alkylthiono, arylthiono, arylsulfonylamine, sulfonic acid, alkysulfonyl, sulfonamido, aryloxy and the like. The substituent may be further substituted by hydroxy, halo, alkyl, alkoxy, alkenyl, alkynyl, aryl or aralkyl.

The term "heteroaryl" refers to an optionally substituted, aromatic group for example, which is a 4 to 7 membered monocyclic, 7 to 11 membered bicyclic, or 10 to 15 membered tricyclic ring system, which has at least one heteroatom and at least one carbon atom-containing ring, for example, pyridine, tetrazole, indazole. This is in contrast to a homoaryl ring in which all atoms in the ring itself are carbon.

The term "alkenyl" refers to straight or branched chain hydrocarbon groups of 2 to 20 carbon atoms, preferably 2 to 15 carbon atoms, and most preferably 2 to 8 carbon atoms, having one to four double bonds.

The term "substituted alkenyl" refers to an alkenyl group substituted by, for example, one to two substituents, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino, indolyl, imidazolyl, furyl, thienyl, thiazolyl, pyrrolidyl, pyridyl, pyrimidyl and the like.

The term "alkynyl" refers to straight or branched chain hydrocarbon groups of 2 to 20 carbon atoms, preferably 2 to 15 carbon atoms, and most preferably 2 to 8 carbon atoms, having one to four triple bonds.

The term "substituted alkynyl" refers to an alkynyl group substituted by a substituent, examples include; halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino and heterocyclyl, e.g. imidazolyl, furyl, thienyl, thiazolyl, pyrrolidyl, pyridyl, pyrimidyl and the like.

The term "cycloalkyl" refers to an optionally substituted, saturated or unsaturated cyclic hydrocarbon ring systems, preferably containing 1 to 3 rings and 3 to 7 carbons per ring, which may be further fused with additional saturated or unsaturated $C_3$-$C_7$ carbocyclic rings. Exemplary groups include cyclopropyl, cyclobutyl, cyclopentyl, cyclohexyl, cycloheptyl, and adamantyl. If substituted, exemplary elements for substitution include but are not limited to: one or more alkyl, alkenyl, or alkynyl groups (which may also be substituted) as described above.

The terms "heterocycle", "heterocyclic" and "heterocyclyl" refer to an optionally substituted, fully saturated or unsaturated, nonaromatic cyclic group, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized. This is in contrast to a homocyclic ring in which all atoms of the ring itself are carbon.

The term "heteroatoms" shall include oxygen, sulfur and nitrogen.

The compounds of the invention may form salts which are also within the scope of this invention. Pharmaceutically acceptable (i.e. non-toxic, physiologically acceptable) salts are preferred, although other salts are also useful, e.g., in isolating or purifying the compounds of this invention.

The compounds of the invention may form salts with alkali metals such as sodium, potassium and lithium, with alkaline earth metals such as calcium and magnesium, with organic bases such as dicyclohexylamine, tributylamine, pyridine and amino acids such as arginine, lysine and the like. Such salts can be formed as known to those skilled in the art.

The compounds of the invention may form salts with a variety of organic and inorganic acids. Such salts include those formed with hydrogen chloride, hydrogen bromide, methanesulfonic acid, sulfufric acid, acetic acid, trifluoroacetic acid, oxalic acid, maleic acid, benzenesulfonic acid, toluenesulfonic acid and various others (e.g., nitrates, phosphates, borates, tartrates, citrates, succinates, benzoates, ascorbates, salicylates and the like). Such salts can be formed as known to those skilled in the art.

In addition, zwitterions may be formed.

All stereoisomers of the compounds of the instant invention are contemplated, either in admixture or in pure or substantially pure form. The definition of compounds according to the invention includes all the possible stereoisomers and their mixtures. Particularly preferred are the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

Uses of the $H_2S$ Releasing Agents of the Invention

Hydrogen sulfide is naturally produced in small amounts by some cells of the mammalian body and has a number of biological functions, including biological signaling. As such, the agents of the invention may be used to treat a wide variety of diseases or conditions that can be cured or improved by increasing the level or amount of $H_2S$ in one or more locations in a patient or subject with the disease or condition.

For example, like nitric oxide, hydrogen sulfide is involved in the relaxation of smooth muscle. Due to his property, hydrogen sulfide is now recognized as potentially treating or protecting against cardiovascular disease [Lefer, David J. (November 2007). "A new gaseous signaling molecule emerges: Cardioprotective role of hydrogen sulfide". PNAS 104 (46): 17907-17908.], with the added benefit that, in contrast to nitric oxide, $H_2S$ does not have the potential to form harmful peroxides by interacting with superoxide. The agents of the invention, with their sustained, controllable release mechanism, are highly amenable to use in such applications. Some evidence suggests that nitric oxide is largely responsible for relaxation of large vessels and hydrogen sulfide is responsible for similar action in smaller blood vessels ("Toxic Gas, Lifesaver", Scientific American, March 2010), allowing combination therapies in which NO and $H_2S$ are simultaneously (or sequentially) administered in a manner that targets muscle relaxation of both large and small blood vessels, as needed, e.g. in ratios that can be tailored to fit the specific needs of a patient, disease, syndrome, etc.

Also in common with nitric oxide, this property of $H_2S$ also provides opportunities for the therapeutic treatment of erectile dysfunction [di Villa Biancaa et. Al. (2009). "Hydrogen sulfide as a mediator of human corpus cavernosum smoothmuscle relaxation". PNAS 106 (11): 4513-4518].

It is known that in Alzheimer's disease, the brain's hydrogen sulfide concentration is severely decreased [Ko et al. (2002-05-24). "Brain hydrogen sulfide is severely decreased in Alzheimer's disease". Biochemical and Biophysical Research Communications 293 (5): 1485-1488]. Thus, administration of the agents of the invention can be used to reverse this condition, and hence to treat symptoms of Alzheimer's.

Due to the ability of $H_2S$ to relax smooth muscle, the compounds of the invention may be used to treat or prevent disease or conditions which involve the circulatory system, blood flow (or lack thereof), abnormal blood pressure, oxygen deprivation, etc. Administration of the agents and the subsequent generation and release of $H_2S$ within the patient cause relaxation of smooth muscle, causing larger volumes of blood to circulate and thereby increasing delivery of $O_2$ within the body. In some embodiments, the agents are used to treat or prevent reperfusion injury, hemorrhagic shock, or hypoxic or ischemic conditions. For example, the compounds of the invention may be used to treat patients that have undergone, are undergoing, or, are susceptible to injury, trauma or critical care treatment. Injury may be caused by external insults, such as burns, wounds, amputations, gunshot wounds, surgical trauma, abdominal surgery, prostate surgery, limb surgery, internal insults (such as septic shock), stroke or cardiac arrest, heart attack that result in the acute reduction in circulation, reductions in circulation due to non-invasive stress (such as exposure to cold or radiation), altitude sickness, or the like. At the cellular level, injury may result in exposure of cells, tissues and/or organs to hypoxia thereby resulting in induction of programmed cell death, or apoptosis. The compounds of the invention are also useful for prevention or treatment of hypoxic or ischemic injury related to transplantation of a tissue or an organ. The compounds of the invention are also useful in the prevention or treatment of delayed graft function.

Such conditions may result in or cause (at least in part) or be or be caused by one or more of the following, which can also be treated or prevented by use of the agents disclosed herein: myocardial infarction, sepsis, vascular abnormalities, cirrhosis, liver injury, kidney injury, vascular calcification, gastric injury induced by drug treatment, burns, lung injury, neutrophil adhesion, leukocyte-mediated inflammation, erectile dysfunction, irritable bowel syndrome, anti-nociceptive effects in post-inflammatory hypersensitivity, acute coronary syndrome, cardiac arrest, planned cardiac bypass surgery, congestive heart failure, neonatal hypoxia/ischemia, myocardial ischemic reperfusion injury, unstable angina, post-angioplasty, aneurysm, trauma, stroke, hemorrhagic shock, and/or blood loss, or the like, and the agents of the invention may be used to prevent or to treat any of these conditions. A therapeutically effective dose of the compounds of the invention is administered to the patient before, after, or both before and after e.g. myocardial infarction, cardiac arrest or stroke. Reperfusion injury can occur following myocardial reperfusion after an acute myocardial infarction, stroke, cardiac arrest, or coronary artery bypass graft (CABG) surgery. Reperfusion injury is noted following the transplantation of an organ or following resuscitation after hemorrhagic shock or severe bleeding in traumatized patients.

The compounds of the invention may also be used to treat hypertension (high blood pressure).

The compounds of the invention are also useful for inducing tissue regeneration and wound healing by prevention/delay of biological processes that may result in delayed wound healing and tissue regeneration. Where there is a substantial wound to the limb or organism, treating the injured area with the compounds of the invention aids in the wound healing and tissue regeneration process by managing the biological processes that inhibit healing and regeneration.

The compounds of the invention are also useful for reducing the risk of trauma from emergency surgical procedures, such as thoroacotomy, laparotomy, and splenic transaction or cardiac surgery, aneurysm, surgery, brain surgery and the like. Where medical attention is not readily available, administration of the compounds of the invention can, for example, provide time for the patient until they can receive other medical attention.

The compounds of the invention may also be used to prevent or treat injury resulting from Systemic Inflammatory Response Syndrome (SIRS), Acute Respiratory Distress Syndrome (ARDS), kidney failure, liver failure and multi-organ failure.

Other methods of using the agents of the invention include pretreating a patient prior to an ischemic or hypoxic injury or disease insult. Such methods are used when an injury or disease, with the potential to cause ischemia or hypoxia, is scheduled or elected in advance, or predicted in advance to likely occur, such as major surgery where blood loss may occur spontaneously or as a result of a procedure. Other anticipated procedures include cardiopulmonary bypass in which oxygenation of the blood may be compromised or vascular delivery of blood may be reduced (as in the setting of coronary artery bypass graft (CABG) surgery). Still other such procedures include treatment of organ donors prior to removal of donor organs for transport and transplantation into a recipient in need of an organ transplant. Other medical conditions include a risk of injury or disease progression is inherent, such as in the context of unstable angina, following angioplasty, bleeding aneurysms, hemorrhagic strokes, following major trauma or blood loss, or congestive heart failure. The risk may be capable of being diagnosed using a medical diagnostic test.

The compounds of the invention may also be used for enhancing survivability and preventing irreversible tissue damage from blood loss or other lack of oxygenation to cells or tissue, such as from lack of an adequate blood supply. Such tissue damage may result from actual blood loss or from conditions or diseases that cause blockage of blood flow to cells or tissue. Reduced blood pressure locally or overall in an organism may also occur, which reduces the amount of oxygen that is carried in the blood, and/or which reduces the number of oxygen carrying cells in the blood. Such conditions and/or diseases include blood clots and embolisms, cysts, growths, tumors, anemia, sickle cell anemia, hemophilia, other blood clotting diseases such as von Willebrand and ITP, atherosclerosis and the like. Such conditions and diseases also include those that create essentially hypoxic or anoxic conditions for cells or tissue in an organism because of an injury, disease, or condition.

The compounds of the invention may also be used to enhance the survivability of and prevent injury or damage to a patient undergoing hemorrhagic shock. The method includes treating the patient at risk of or in a state of hemorrhagic shock with a therapeutically effective dose of the agent, e.g. preferably within about one hour of the injury or sooner. The patient may be transported to a controlled environment, such as surgery, where the initial cause of the injury can be addressed. The patient can then be brought back to normal function in a controlled manner. The first hour after injury, referred to as the golden hour, can be critical to a successful outcome.

The compounds of the invention may be used to treat or prophylactically treat various diseases and disorders such as those disclosed in U.S. Patent Application Publication No. 2008/0199541, including, for example: myocardial infarction, sepsis (Hui, et al. J Infect (2003) 47:155-160), congestive heart failure, vascular abnormalities in cirrhosis (Fiorucci S, et al., Hepatology (2005) 42:539-548), as a cardioprotectent (Geng, et al., Biochem Biophys Res Commun (2004) 313:362-368), as a neuroprotectant (Qu K. et al, Stroke (2006) 37:889-893), myocardial ischemia reperfusion injury (Johansen et al., Basic Res Cardiol (2006) 101:53-60), vascular calcification (Wu et al., Acta Pharmacol Sin. (2006) 27:299-306), gastric injury induced by drug treatment (Fiorucci, S. et al., Gastroenterology (2005) 129:1210-1224), neutrophil adhesion and modulation of leukocyte-mediated inflammation (Zanardo et al., FASEB J. (2006) 20:2118-2120), erectile dysfunction (Srilatha B. et al., Eur J. Pharmacol. (2006) 535:280-282), irritable bowel syndrome (Distrutti E., et al., JPET (2006) 319:447-458), and, anti-nociceptive effects in post-inflammatory hypersensitivity (ibid.).

Other methods in which the agents of the invention may be used include those described in, for example, US patent applications 20080003 18 and 20080226750, e.g. to induce apnea, treat shock, etc. In addition, US patent application 20110195945 describes methods and compositions for treating or preventing disease or injury to a human patient or biological material undergoing ischemic or hypoxic conditions, in which the agents of the invention may be employed instead of or in addition to (e.g. with) the compounds described therein. The complete contents these and other references, patents and patent applications referenced herein are hereby incorporated by reference in entirely.

In some embodiments, the $H_2S$ delivery agents of the invention are used to induce stasis in tissues, cells or organisms, e.g. as described in issued U.S. Pat. No. 7,993,681 to Roth, and associated US patent applications 20080271726, 20080171725, 20080171093, 2008085329, 20070078113, 20050170019, 2005147692, and 20050136125, the complete contents of each of which are hereby incorporated by reference. '681 describes induction of stasis in tissue that are e.g. not contained within an organism ("isolated tissue"), and is based on the use of $O_2$ antagonists such as $H_2S$ that were determined to have a protective function, and which thus serve as protective agents of tissues. The stasis is advantageously reversible. Such compounds can be used in methods, articles of manufacture, and apparatuses to protect, preserve, and/or extend the longevity of cells or tissue used e.g. for transfusion or transplantation (therapeutic applications, including organ transplants); for research purposes; for screening assays to identify, characterize, or manufacture other compounds that induce stasis; for testing a sample from which the tissue was obtained (diagnostic applications); for preserving or preventing damage to the tissue that will be placed back into the organism from which they were derived (preventative applications); and for preserving or preventing damage to them during transport or storage. The compounds of the invention may also be used to enhance the survivability of ex vivo biological matter (such as isolated cells, tissues and organs) subjected to hypoxic or ischemic conditions. Other such ex vivo biological material include platelets and other blood products as well as tissues and organs to be transplanted. As such, the compounds of the invention may also be used to enhance survivability of biological material in the laboratory or research context, such as where cell lines or laboratory organisms are purposefully subjected to hypoxic or ischemic conditions, such as during cryopreservation and storage. Cells, tissues or organs may also be stored or transported in the presence of the compounds of the invention. The compounds of the invention may also be used to increase the survivability of donor tissues and organs extending the time before the donor tissue is transplanted into a recipient and blood flow is restored. Such methods may be combined with known preservation methods and materials, such as preservation agents and oxygen perfusion. Methods of using the compounds of the invention provide a way of enhancing survivability of platelets stored in an anoxic environment by treating the platelets with a therapeutically effective dose of the compounds of the invention during storage. The compounds of the invention are also useful for preserving both non-living biological material and preserving or extending the shelf-life of non-biological material by treating the non-living biological matter or non-biological.

Compositions and Administration

The compounds of the invention may be formulated into various dosage forms for various routes of administration for treating e.g. tissues, organs, limbs and even whole organisms with a therapeutically effective dose of one or more (i.e. at least one) of the compounds to protect such from the detrimental effects of injury or disease.

Administration of the compounds of the invention, or their pharmaceutically acceptable salts, in pure form or in an appropriate pharmaceutical composition, can be carried out via any of the accepted modes of administration of agents for serving similar utilities. The pharmaceutical compositions of the invention can be prepared by combining a compound (or more than one compound) of the invention with an appropriate pharmaceutically acceptable carrier, diluent or excipient, and may be formulated. The terms "parenteral carrier system" (including variations thereof such as the various specific injectable and infusible dosage forms) refer to compositions comprising one or more pharmaceutically suitable excipients, such as solvents (e.g. water) and co-solvents, solubilizing agents, wetting agents, suspending agents, thickening agents, emulsifying agents, chelating agents, buffers, pH adjusters, antioxidants, reducing agents, antimicrobial preservatives, bulking agents, protectants, tonicity adjusters, and special additives. In addition, other therapeutic agents may be added to the composition, if desirable.

The term "parenteral" as used herein includes subcutaneous injections, intravenous, intramuscular, intrastemal injection or infusion techniques. Pharmaceutical compositions of the invention are formulated so as to allow the active ingredients contained therein to be bioavailable upon administration of the composition to a patient.

Several distinct classes of injectable dosage forms exist as defined by the USP: emulsions, lipids, powders, solutions and suspensions. Emulsion injection includes an emulsion comprising a sterile, pyrogen-free preparation intended to be administered parenterally. Lipid complex and powder for solution injection are sterile preparations intended for reconstitution to form a solution for parenteral use.

Powder for suspension injection is a sterile preparation intended for reconstitution to form a suspension for parenteral use. Powder lyophilized for liposomal suspension injection is a sterile freeze dried preparation intended for reconstitution for parenteral use that is formulated in a manner allowing incorporation of liposomes, such as a lipid bilayer vesicle having phospholipids used to encapsulate an active drug substance within a lipid bilayer or in an aqueous space, whereby the formulation may be formed upon reconstitution.

Powder lyophilized for solution injection is a dosage form intended for the solution prepared by lyophilization ("freeze drying"), whereby the process involves removing water from products in a frozen state at extremely low pressures, and whereby subsequent addition of liquid creates a solution that conforms in all respects to the requirements for injections. Powder lyophilized for suspension injection is a liquid preparation intended for parenteral use that contains solids suspended in a suitable fluid medium, and it conforms in all respects to the requirements for sterile suspensions, whereby the medicinal agents intended for the suspension are prepared by lyophilization.

Solution injection involves a liquid preparation containing one or more drug substances dissolved in a suitable solvent or mixture of mutually miscible solvents that is suitable for injection. Solution concentrate injection involves a sterile preparation for parenteral use that, upon addition of suitable solvents, yields a solution conforming in all respects to the requirements for injections.

Suspension injection involves a liquid preparation (suitable for injection) containing insoluble solid and/or immiscible liquid particles dispersed throughout a liquid phase. Suspension liposomal injection is a liquid preparation (suitable for injection) having an oil phase dispersed throughout an aqueous phase in such a manner that liposomes (a lipid bilayer vesicle usually containing phospholipids used to encapsulate an active drug substance either within a lipid bilayer or in an aqueous space) are formed. Suspension sonicated injection is a liquid preparation (suitable for injection) containing solid particles dispersed throughout a liquid phase, whereby the particles are insoluble. In addition, the product may be sonicated as a gas is bubbled through the suspension resulting in the formation of microspheres by the solid particles.

The parenteral carrier system includes one or more pharmaceutically suitable (i.e., USP and FDA-approved) excipients and/or diluents, such as solvents and co-solvents, solubilizing agents, wetting agents, suspending agents, thickening agents, emulsifying agents, chelating agents, buffers, pH adjusters, antioxidants, reducing agents, antimicrobial preservatives or other preservatives, dispersing agents, surfactant, bulking agents, protectants, tonicity adjusters, emulsifiers, stabilizers, glidants, isotonic agents, and special additives.

The compositions of the invention typically contain the agents of the invention in an amount that is sufficient to prevent or treat the condition/disease of interest. While any suitable amount of agent may be present in a composition, the amount generally ranges from about 1-99% by weight of all ingredients.

The terms "therapeutically effective dose" (and variations thereof) refer to an amount, dose or dosing regimen of a compound (i.e., active pharmaceutical ingredient, prodrug or precursor thereof) that upon interaction with a biological material is sufficient to treat or prevent injury of a biological material (e.g., induce a measurable result) exposed to hypoxic or ischemic conditions, whereby such dose may vary depending on the form of the compound, the biological material's condition and/or severity, the route of administration, the age of the biological material, and the like.

"Therapeutically effective dose" may also mean a dose administered to a human subject/patient in a controlled Phase II or Phase III clinical trial that causes a statistically significant benefit on a predefined clinical endpoint (e.g., mortality). A therapeutically effective dose may also be a dose that enhances the survivability of biological matter in response to a disease or injury or an amount that induces stasis or pre-stasis in the biological matter.

For the treatment of living animals, the agents of the invention are typically administered in a dose in the range of from about 0.1 mg/kg to about 300 mg/kg, and preferably in a dose in the range of from about 0.1 mg/kg to about 50 mg/kg of body weight. This usually results in a concentration in the circulation of the recipient of from about 10 µM to about 300 µM, e.g. less than about 500 µM Those of skill in the art will recognize that suitable doses and suitable protocols for administering drugs (e.g. the frequency of administration, the mode of administration, the duration of the treatment period, etc.) are often determined during Clinical Trials, and are best selected by a skilled medical practitioner, e.g. a physician.

If the biological material is not a living animal, but is instead e.g. a tissue for transplantation, the dose range may be somewhat higher (e.g. about 10 µM to about 500 µM), so long as prior to transplantation, the levels are lowered to an extent that does not harm the recipient. If the tissue or cells are used for purely research purposes, then the levels may be higher, e.g. a concentration of from about 10 µM to about 1000 µM, or as high as necessary to maximize the effects that is being sought. The instant dosage form and routes of administration of a pharmaceutical composition include parenteral by injection or infusion (or other parenteral) such as intravenous, injection, infusion, continuous infusion, intradermal, intraarterial, intracerebral, intracerebroventricular, intracardiac, intraosseous infusion, intralesional, intracranial, intraprostatatical, intrapleural, intratracheal, intranasal, intravitreal, intravaginal, intrarectal, intratumoral, intramuscular, intraocular, intrathecal, subcutaneous, subconjunctival, transmucosal, intramuscular, intravesicular, intravesical, intracavernosal injection, intrapericardial, intraumbilical, intraocularal, absorption, adsorption, immersion, localized perfusion, intracisternal, epidural, etc. The compounds of the invention may be administered to the biological material in a dose and for a duration sufficient to protect the biological material from one or more of the following: damage or death resulting from the injury; onset or progression of disease; hemorrhaging in the biological material, or the like.

The mammalian biological material may be one or more of the following: cells, tissues, organs, organisms or an animal. The mammal may be a human, although this need not always be the case, as veterinary applications are also contemplated. The biological material may be used for transplantation. Administration may be on any desired schedule appropriate for the particular form of the agent and the condition or disease being addressed, as determined by a skilled medical practitioner.

In other embodiments, the compounds of the invention may have non-biological applications. For example, the agents of the invention or $H_2S$ produced from the agent of the invention may be used for the synthesis of other compounds, e.g. alkali metal sulfides and metal sulfides, or for separating heavy (deuterium containing) water in the Girdler sulfide (GS) process, or in other manufacturing or industrial processes.

Methods

The invention also provides methods of using the agents described herein. Exemplary methods include but are not limited to, for example, therapeutic methods in which one or more of the agents is administered in order to prevent or treat a condition or disease that can be cured or ameliorated by administration of the agent(s). Exemplary diseases/conditions are described above. The method can involve the steps of identifying a patient or subject with the disease or condition of interest, determining a suitable dosage of the agent(s), and administering the agent(s) to the subject/patient. Further, the methods may involve monitoring the response of the patient to the drug, and/or the outcome of treatment, and the modification of the original protocol as needed. Those of skill in the art will recognize that, in some embodiments, the outcome may be a cure in that all disease symptoms disappear and do not return for at least a period of time. However, in other cases, administration may be ongoing in order to keep the condition or disease "in check", i.e. to keep the occurrence of symptoms to an acceptable level, or at least to a level that is lower than that experienced by the patient in the absence of treatment. Even a partial lessening of symptoms may be highly beneficial.

In addition, the agents of the invention may be administered in conjunction with the administration of other therapies or therapeutic agents, e.g. other agents suitable for treating the disease or condition which the agent is intended treat or prevent.

It should be emphasized that the above-described embodiments and following specific examples of the present invention, particularly, any "preferred" embodiments, are merely possible examples of implementations, merely set forth for a clear understanding of the principles of the invention. Many variations and modifications may be made to the above-described embodiment(s) of the invention without departing substantially from the spirit and principles of the invention. All such modifications and variations are intended to be included herein within the scope of this disclosure and the present invention and protected by the following claims.

The complete contents of all references, publications, patents and patent applications cited herein are hereby incorporated by reference in entirety.

EXAMPLES

Example 1

Synthesis

Scheme 2: General synthetic Method for Compounds 2-13.

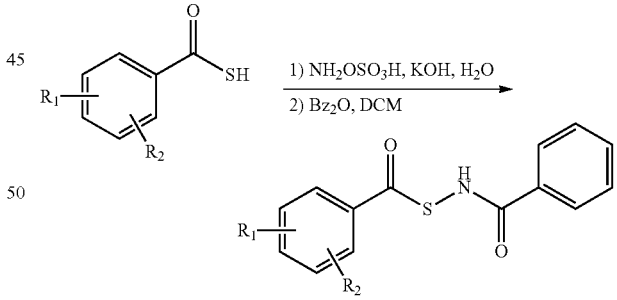

To a stirred solution of KOH (560 mg, 10 mmol) in water (15 mL) was added thiobenzoic acid (690 mg, 5 mmol) and hydroxylamine-O-sulfonic acid (565 mg, 5 mmol). The solution was stirred for 20 min at rt. The white solid (S-benzoylthiohydroxylamine) was collected by filtration and then dissolved in $CH_2Cl_2$ (10 mL). To this mixture was added benzoic anhydride (2.26 g, 10 mmol). The resulting solution was allowed to stir overnight at rt. The crude product was purified by recrystallization ($CH_2Cl_2$/hexane) to give 2 as white solid. m.p. 138-140° C.; $^1H$ NMR (300 MHz, $CDCl_3$) δ 7.92 (m, 4H), 7.60 (m, 1H), 7.53 (m, 1H), 7.39 (m, 4H), 7.17 (s, 1H); $^{13}C$ NMR (75 MHz, $CDCl_3$) δ 190.0, 159.1, 134.6, 134.4, 133.3, 132.8, 129.3, 129.0, 128.0, 127.3; IR (thin film) cm$^{-1}$ 3265, 3062, 1696, 1659, 1451, 1419, 1257, 1207; HRMS m/z 258.0598 [M+H]$^+$; calcd for C$_{14}$H$_{12}$NO$_2$S 258.0589; overall yield: 64% (2 steps).

3 was prepared from p-fluorothiobenzoic acid using the same procedure as 2. m.p. 143-145° C.; $^1$H NMR (300 MHz, CDCl$_3$) δ 7.88 (m, 4H), 7.61 (s, 1H), 7.50 (tt, J=7.5 Hz, J=1.5 Hz 1H), 7.39 (t, J=7.8 Hz, 2H), 7.12 (t, J=8.7 Hz, 2H); $^{13}$C NMR (75 MHz, CDCl$_3$) δ 189.7, 168.9, 133.0, 132.8, 130.7, 130.0, 129.9, 128.9, 128.1, 116.7; IR (thin film) cm$^{-1}$ 3241, 1693, 1652, 1595, 1453, 1428, 1208, 1100, 908, 851; HRMS m/z 276.0504 [M+H]$^+$; calcd for C$_{14}$H$_{11}$FNO$_2$S 276.0495; overall yield: 36% (2 steps).

4 was prepared from p-trifluoromethylthiobenzoic acid using the same procedure as 2. m.p. 163-164° C.; $^1$H NMR (300 MHz, CD$_3$OD) δ 8.02 (d, J=7.8 Hz, 2H), 7.92 (d, J=7.5 Hz, 2H), 7.76 (d, J=8.1 Hz, 2H), 7.58 (t, J=7.5 Hz, 1H), 7.48 (t, J=7.5 Hz, 2H), 7.20 (s, 1H); $^{13}$C NMR (75 MHz, CD$_3$OD) δ 190.1, 170.3, 137.7, 133.2, 132.6, 128.6, 128.0, 127.5, 126.2, 126.1; IR (thin film) cm$^{-1}$ 3199, 1705, 1649, 1456, 1407, 1326, 1170, 1125, 1067, 905, 846; HRMS m/z 326.0471 [M+H]$^+$; calcd for C$_{15}$H$_{11}$F$_3$NO$_2$S 326.0463; overall yield: 27% (2 steps).

5 was prepared from m-chlorothiobenzoic acid using the same procedure as 2. m.p. 130-132° C.; $^1$H NMR (300 MHz, CDCl$_3$) δ 7.91 (m, 2H), 7.86 (t, J=2.0 Hz, 1H), 7.77 (dt, J=7.8 Hz, J=1.2 Hz 1H), 7.57 (m, 2H), 7.45 (m, 3H), 7.33 (s, 1H); $^{13}$C NMR (75 MHz, CDCl$_3$) δ 190.0, 168.8, 135.8, 135.6, 134.5, 133.0, 132.9, 130.6, 129.0, 128.0, 127.3, 125.4; IR (thin film) cm$^{-1}$ 3278, 1702, 1660, 1452, 1421, 1260, 1198; HRMS m/z 292.0207 [M+H]$^+$; calcd for C$_{14}$H$_{11}$ClNO$_2$S 292.0199; overall yield: 42% (2 steps).

6 was prepared from o-methylthiobenzoic acid using the same procedure as 2. m.p. 101-103° C.; $^1$H NMR (300 MHz, CDCl$_3$) δ 7.93 (d, J=8.7 Hz, 2H), 7.76 (d, J=8.1 Hz, 1H), 7.69 (s, 1H), 7.49 (m, 1H), 7.40 (m, 3H), 7.25 (t, J=7.5 Hz, 2H), 2.47 (s, 3H); $^{13}$C NMR (75 MHz, CDCl$_3$) δ 193.1, 168.8, 138.1, 133.8, 133.2, 133.0, 132.7, 132.2, 128.9, 128.4, 128.1, 126.3, 20.8; IR (thin film) cm$^{-1}$ 3252, 3071, 1687, 1453, 1424, 1326, 1292, 896, 708; HRMS m/z 272.0759 [M+H]$^+$; calcd for C$_{15}$H$_{14}$NO$_2$S 272.0745; overall yield: 68% (2 steps).

7 was prepared from m-methylthiobenzoic acid using the same procedure as 2. m.p. 79-81° C.; $^1$H NMR (300 MHz, CDCl$_3$) δ 8.11 (d, J=7.5 Hz, 1H), 7.93 (d, J=7.5 Hz, 2H), 7.73 (s, 2H), 7.50 (m, 4H), 7.06 (s, 1H), 2.43 (s, 3H); $^{13}$C NMR (75 MHz, CDCl$_3$) δ 191.5, 169.2, 139.1, 135.3, 134.4, 133.0, 132.6, 129.0, 128.8, 128.2, 127.7, 124.5, 21.5; IR (thin film) cm$^{-1}$ 3258, 2911, 1693, 1661, 1450, 1418, 1245; HRMS m/z 272.0741 [M+H]$^+$; calcd for C$_{15}$H$_{14}$NO$_2$S 272.0745; overall yield: 71% (2 steps).

8 was prepared from p-methylthiobenzoic acid using the same procedure as 1 m.p. 135-137° C.; $^1$H NMR (300 MHz, CDCl$_3$) δ 7.93 (m, 2H), 7.82 (d, J=8.4 Hz, 2H), 7.57 (m, 1H), 7.48 (m, 2H), 7.29 (d, J=8.1 Hz, 2H), 7.10 (s, 1H), 2.43 (s, 3H); $^{13}$C NMR (75 MHz, CDCl$_3$) δ 190.8, 168.9, 145.7, 133.2, 132.7, 131.8, 129.9, 128.9, 128.0, 127.4, 22.1; IR (thin film) cm$^{-1}$ 3264, 2923, 1695, 1659, 1601, 1420, 1209, 1177, 903; HRMS m/z 272.0736 [M+H]$^+$; calcd for C$_{15}$H$_{14}$NO$_2$S 272.0745; overall yield: 66% (2 steps).

9 was prepared from o-methoxythiobenzoic acid using the same procedure as 2. m.p. 123-124° C.; $^1$H NMR (300 MHz, CDCl$_3$) δ 7.5 (m, 3H), 7.53 (m, 2H), 7.44 (m, 3H), 7.04 (m, 2H), 3.98 (s, 3H); $^{13}$C NMR (75 MHz, CDCl$_3$) δ 189.5, 160.1, 135.5, 133.7, 133.1, 132.4, 130.2, 128.9, 127.9, 123.1, 121.4, 112.0, 56.1; IR (thin film) cm$^{-1}$ 3279, 1654, 1597, 1485, 1452, 1434, 1288, 1247, 1111, 1016, 905; HRMS m/z 288.0535 [M+H]$^+$; calcd for C$_{15}$H$_{14}$NO$_3$S 288.0694; overall yield: 63% (2 steps).

10 was prepared from m-methoxythiobenzoic acid using the same procedure as 2. m.p. 78-80° C.; $^1$H NMR (300 MHz, CDCl$_3$) δ 7.90 (m, 2H), 7.79 (s, 1H), 7.44 (m, 2H), 7.32 (m, 4H), 7.11 (m, 1H), 3.79 (s, 3H); $^{13}$C NMR (75 MHz, CDCl$_3$) δ 191.2, 169.0, 160.1, 135.6, 133.1, 132.7, 130.3, 128.9, 128.1, 121.0, 119.7, 111.4, 55.7; IR (thin film) cm$^{-1}$ 3260, 1696, 1663, 1597, 1582, 1452, 1426, 1260, 786, 693; HRMS m/z 288.0512 [M+H]$^+$; calcd for C$_{15}$H$_{14}$NO$_3$S 288.0694; overall yield: 60% (2 steps).

11 was prepared from p-methoxythiobenzoic acid using the same procedure as 2. m.p. 131-132° C.; $^1$H NMR (300 MHz, CDCl$_3$) δ 7.90 (m, 4H), 7.53 (m, 1H), 7.45 (m, 2H), 7.22 (s, 1H), 6.95 (m, 2H), 3.78 (s, 3H); $^{13}$C NMR (75 MHz, CDCl$_3$) δ 189.3, 164.7, 140.9, 133.4, 132.7, 129.6, 129.0, 128.0, 127.1, 114.5, 55.8; IR (thin film) cm$^{-1}$ 3264, 1657, 1601, 1508, 1452, 1419, 1262, 1169, 903; HRMS m/z 288.0710 [M+H]$^+$; calcd for C$_{15}$H$_{14}$NO$_3$S 288.0694; overall yield: 66% (2 steps).

12 was prepared from 2,4-dimethoxythiobenzoic acid using the same procedure as 2. m.p. 138-139° C.; $^1$H NMR (300 MHz, CDCl$_3$) δ 7.92 (m, 3H), 7.47 (m, 4H), 6.57 (d, J=2.4 Hz, 1H), 6.46 (d, J=2.4 Hz, 1H), 3.99 (s, 3H), 3.86 (s, 3H); $^{13}$C NMR (75 MHz, CDCl$_3$) δ 188.0, 169.1, 165.9, 161.9, 133.9, 132.3, 132.2, 128.9, 127.9, 116.6, 106.7, 98.1, 56.0, 55.9; IR (thin film) cm$^{-1}$ 3241, 2942, 1648, 1601, 1453, 1421, 1252, 1217, 1126, 1021; HRMS m/z 318.0751 [M+H]$^+$; calcd for C$_{16}$H$_{16}$NO$_4$S 318.0800; overall yield: 56% (2 steps).

13 was prepared from p-N,N-dimethylthiobenzoic acid using the same procedure as 2. m.p. 192-194° C.; NMR (300 MHz, DMSO-d$_6$) δ 9.87 (s, 1H), 7.96 (d, J=8.4 Hz, 2H), 7.73 (d, J=9.0 Hz, 2H), 7.61 (t, J=6.9 Hz, 1H), 7.52 (t, J=7.8 Hz, 2H), 6.77 (d, J=9.3 Hz, 2H), 3.03 (s, 6H); $^{13}$C NMR (75 MHz, DMSO-d$_6$) δ 187.8, 168.8, 154.7, 134.0, 132.9, 129.2, 128.7, 121.2, 111.8, 40.3; IR (thin film) cm$^{-1}$ 3267, 1679, 1648, 1449, 1414, 1240, 889, 815; HRMS m/z 301.1009 [M+H]; calcd for C$_{16}$H$_{17}$N$_2$O$_2$S 301.1011; overall yield: 69% (2 steps).

Scheme 3: Synthesis of 14

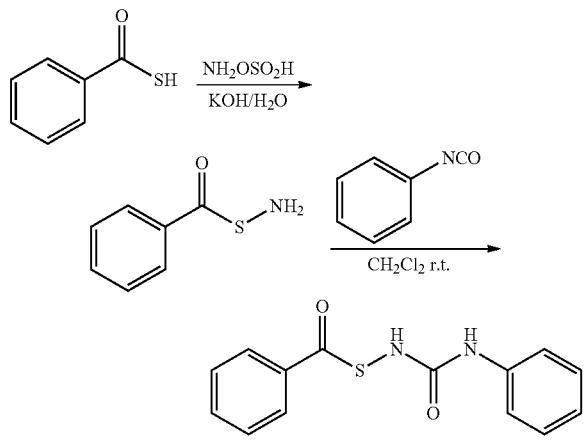

To a stirred solution of KOH (560 mg, 10 mmol) in water (15 mL) was added thiobenzoic acid (690 mg, 5 mmol) and hydroxylamine-O-sulfonic acid (565 mg, 5 mmol). The solution was stirred for 20 min at room temperature. The white solid (S-benzoylthiohydroxylamine) was collected by filtration and then dissolved in CH$_2$Cl$_2$ (10 mL). To this mixture was added phenyl isocyanate (1.19 g, 10 mmol). The resulting solution was allowed to stir overnight at room temperature. The crude product was collected by the filtration and recrystallized in CH$_2$Cl$_2$/hexane. Pure compound 14 was obtained as a white solid (overall yield 60%). m.p. 184-186° C.; $^1$H NMR (300 MHz, DMSO-d$_6$) δ 9.11 (s, 1H), 7.99 (s, 1H), 7.88 (d, 7.5 Hz, 2H), 7.74 (t, J=8.1 Hz, 1H), 7.59 (t, J=7.5 Hz, 2H), 7.45 (d, J=7.5 Hz, 2H), 7.24 (t, J=7.8 Hz, 2H), 6.98 (t, J=7.2 Hz, 1H); $^{13}$C NMR (75 MHz, DMSO-d$_6$) δ 193.4, 155.0, 140.1, 135.2, 134.6, 130.1, 129.4, 127.2, 123.1, 119.3; IR (thin film) cm$^{-1}$ 3286, 3240, 1697, 1638, 1541, 1474, 1459, 1207; MS m/z 273.1 [M+H]$^+$; calcd for C$_{14}$H$_{13}$N$_2$O$_2$S 273.1.

Scheme 4: Synthesis of 15

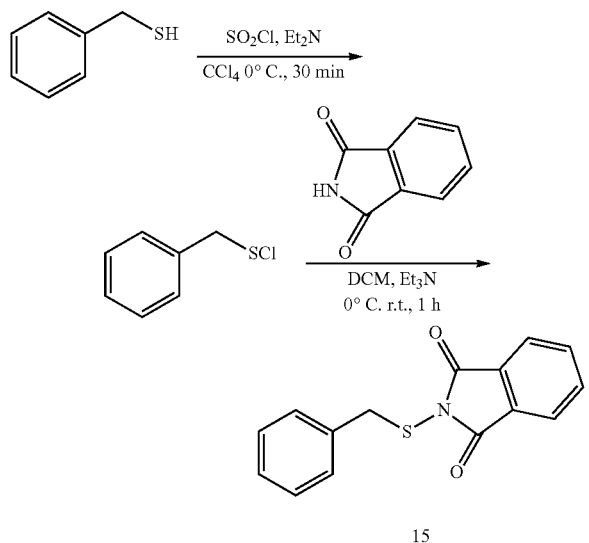

15

Benzyl thiol (620 mg, 5 mmol) and Et$_3$N (0.1 mL) were added to CCl$_4$, followed by the addition of SO$_2$Cl$_2$ (709 mg, 5.25 mmol). The mixture was stirred at 0° C. for 30 minutes. CCl$_4$ was then removed by evaporation. The resulted solid residue was dissolved in CH$_2$Cl$_2$ (5 mL). This solution was then added into a CH$_2$Cl$_2$ (20 mL) solution containing phthalimide (736 mg, 5 mmol) and Et$_3$N (760 mg, 7.5 mmol) at 0° C. The resultant solution was warmed up to room temperature and stirred for 1 hour. Unreacted phthalimide was removed by adding 1M KOH aqueous solution, followed by the extraction with CH$_2$Cl$_2$ (3 times). The organic layers were combined and concentrated. The crude product was recrystallized in CH$_2$Cl$_2$/hexane to give 15 as white solid (overall yield: 22%).

m.p. 164-166° C.; $^1$H NMR (300 MHz, CDCl$_3$) δ 7.85 (m, 2H), 7.74 (m, 2H), 7.27 (m, 2H), 7.21 (m, 3H), 4.11 (s, 2H); $^{13}$C NMR (75 MHz, CDCl$_3$) δ 168.2, 134.7, 134.5, 132.1, 129.7, 128.9, 128.1, 124.0, 42.7; IR (thin film) cm$^{-1}$ 3365, 1744, 1713, 1561, 1541, 1467, 1342, 1287, 1048, 865; MS m/z 270.1 [M+H]$^+$; calcd for C$_{15}$H$_{12}$NO$_2$S 270.1.

Scheme 5: General Synthetic route to compounds 16-18

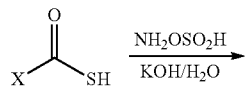

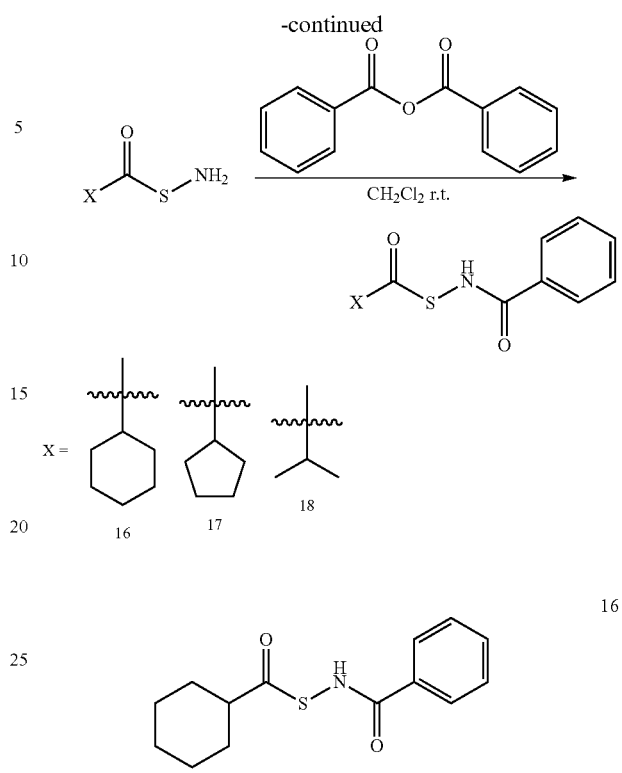

To a stirred solution of KOH (560 mg, 10 mmol) in water (15 mL) was added cyclohexanecarbothioic acid (720 mg, 5 mmol) and hydroxylamine-O-sulfonic acid (565 mg, mmol). The solution was stirred for 20 min at room temperature. The white solid S-(cyclohexanecarbonyl)thiohydroxylamine was collected by filtration and then dissolved in CH$_2$Cl$_2$ (10 mL). To this mixture was added benzoic anhydride (2.26 g, 10 mmol). The resulting solution was allowed to stir overnight at room temperature. The crude product was purified by recrystallization (CH$_2$Cl$_2$/hexane) to give 16 as white solid (overall yield: 65%). m.p. 147-148° C.; $^1$H NMR (300 MHz, CDCl$_3$) δ 7.85 (d, J=8.4 Hz, 2H), 7.53 (t, J=7.2 Hz, 1H), 7.43 (t, J=7.8 Hz, 2H), 7.11 (s, 1H), 2.54 (m, 1H), 1.95 (m, 2H), 1.81 (m, 2H), 1.67 (m, 1H), 1.52 (m, 2H), 1.29 (m, 3H); $^{13}$C NMR (75 MHz, CDCl$_3$) δ 202.0, 168.3, 133.2, 132.6, 128.9, 127.9, 49.4, 29.1, 25.2; IR (thin film) cm$^{-1}$ 3279, 2927, 2857, 1705, 1654, 1552, 1537, 1451, 1416, 966; MS m/z 264.1 [M+H]; calcd for C$_{14}$H$_{18}$NO$_2$S 264.1.

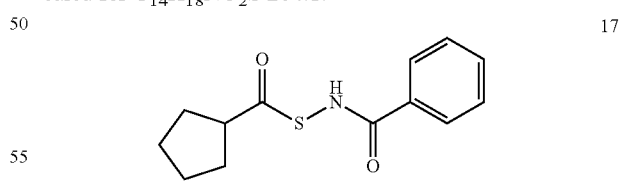

17 was prepared from cyclopentanecarbothioic S-acid using the same procedure as 16. m.p. 126-128° C.; $^1$H NMR (300 MHz, CDCl$_3$) δ 7.86 (d, J=8.7 Hz, 2H), 7.54 (t, J=7.5 Hz, 1H), 7.44 (t, J=7.8 Hz, 2H), 7.09 (s, 1H), 3.01 (quin, J=7.5 Hz, 1H), 1.92 (m, 4H), 1.69 (m, 4H), 1.67 (m, 1H), 1.52 (m, 2H), 1.29 (m, 3H); $^{13}$C NMR (75 MHz, CDCl$_3$) δ 199.5 164.0, 133.2, 132.7, 129.0, 127.9, 49.6, 30.5, 26.2; IR (thin film) cm$^{-1}$ 3286, 2950, 2872, 1701, 1654, 1559, 1541, 1508, 1456, 1419, 994; MS m/z 272.0 [M+Na]$^+$; calcd for C$_{13}$H$_{15}$NNaO$_2$S 272.1; overall yield: 56%.

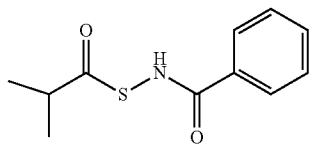

18

18 was prepared from 2-methylpropanethioic S-acid using the same procedure as 16. m.p. 103-106° C.; $^1$H NMR (300 MHz, CDCl$_3$) δ 7.86 (m, 2H), 7.47 (m, 3H), 7.24 (s, 1H), 2.79 (m, 1H), 1.25 (s, 6H); $^{13}$C NMR (75 MHz, CDCl$_3$) δ 203.2, 168.4, 132.7, 130.4, 128.9, 127.9, 40.0, 19.0; IR (thin film) cm$^{-1}$ 3263, 2996, 2927, 1717, 1655, 1561, 1541, 1498, 1452, 1420, 1267, 1248, 970; MS m/z 223.9 [M+H]$^+$; calcd for C$_{11}$H$_{14}$NO$_2$S 224.1; overall yield: 76%.

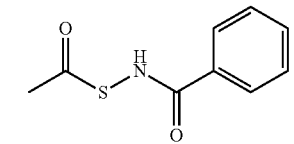

19

19 was prepared from thioacetic acid using the same procedure as 16. m.p. 83-86° C.; $^1$H NMR (300 MHz, CDCl$_3$) δ 7.85 (d, J=8.7 Hz, 2H), 7.54 (t, J=7.5 Hz, 1H), 7.44 (t, J=7.8 Hz, 2H), 7.37 (m, 1H), 2.32 (s, 3H); $^{13}$C NMR (75 MHz, CDCl$_3$) δ 195.6, 168.4, 133.0, 132.8, 129.0, 128.0, 26.5; IR (thin film) cm$^{-1}$ 3261, 1723, 1692, 1664, 1599, 1581, 1452, 1422, 1262, 1099; MS m/z 195.9 [M+H]$^+$; calcd for C$_9$H$_{10}$NO$_2$S 196.0; overall yield: 58%.

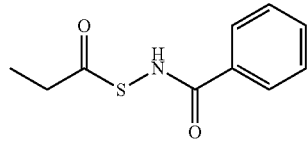

20

20 was prepared from propanethioic S-acid using the same procedure as 16. m.p. 42-44° C.; $^1$H NMR (300 MHz, CDCl$_3$) δ 7.85 (d, J=7.2 Hz, 2H), 7.51 (m, 2H), 7.40 (m, 2H), 2.57 (q, J=7.5 Hz, 2H), 1.19 (t, J=7.2 Hz, 3H); $^{13}$C NMR (75 MHz, CDCl$_3$) δ 199.9, 168.6, 132.7, 130.3, 128.9, 128.0, 33.6, 9.2; IR (thin film) cm$^{-1}$ 3443, 1657, 1500, 1453, 1422, 1263, 1089, 1014; MS m/z 209.9 [M+H]$^+$; calcd for C$_{10}$H$_{12}$NO$_2$S 210.1; overall yield: 71%.

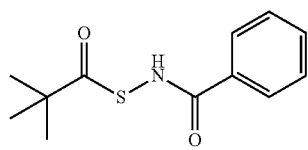

21

21 was prepared from 2,2-dimethylpropanethioic S-acid using the same procedure as 16. m.p. 102-103° C.; $^1$H NMR (300 MHz, CDCl$_3$) δ 7.87 (d, J=7.2 Hz, 2H), 7.53 (t, J=7.8 Hz, 1H), 7.43 (t, J=8.1 Hz, 2H), 7.02 (s, 1H), 1.30 (s, 9H); $^{13}$C NMR (75 MHz, CDCl$_3$) δ 205.6, 168.6, 133.4, 132.6, 128.9, 127.9, 45.5, 26.8; IR (thin film) cm$^{-1}$ 3255, 2966, 2927, 1709, 1662, 1650, 1560, 1541, 1451, 1420, 1365, 1267, 1248, 935; MS m/z 238.0 [M+H]$^+$; calcd for C$_{12}$H$_{16}$NO$_2$S 238.1; overall yield: 69%.

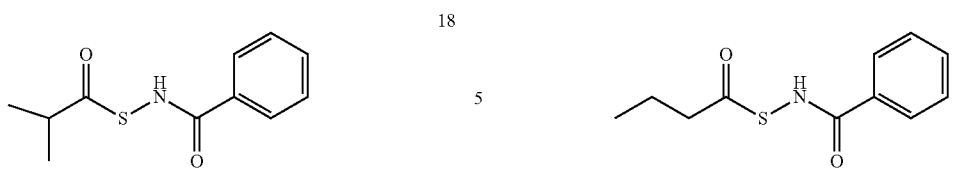

22

22 was prepared from butanethioic S-acid using the same procedure as 16. m.p. 58-61° C.; $^1$H NMR (300 MHz, CDCl$_3$) δ 7.85 (d, J=7.8 Hz, 2H), 7.50 (t, J=7.5 Hz, 2H), 7.40 (d, J=7.8 Hz, 1H), 7.37 (s, 1H), 2.51 (t, J=7.2 Hz, 2H), 1.70 (m, 2H), 0.96 (t, J=7.5 Hz, 3H); $^{13}$C NMR (75 MHz, CDCl$_3$) δ199.0, 168.4, 133.1, 132.7, 128.9, 128.0, 41.9, 18.9, 13.8; IR (thin film) cm$^{-1}$ 3440, 1660, 1453, 1423, 1262, 1110, 982; MS m/z 223.9 [M+H]$^+$; calcd for C$_{11}$H$_{14}$NO$_2$S 224.1; overall yield: 75%.

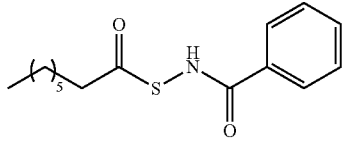

23

23 was prepared from octanethioic S-acid using the same procedure as 16. m.p. 46-48° C.; $^1$H NMR (300 MHz, CDCl$_3$) δ 7.80 (d, J=7.2 Hz, 2H), 7.63 (s, 1H), 7.43 (t, J=7.2 Hz, 1H), 7.35 (t, J=7.8 Hz, 2H), 2.44 (m, 2H), 1.59 (m, 2H), 1.19 (m, 8H), 0.80 (m, 3H); $^{13}$C NMR (75 MHz, CDCl$_3$) δ199.4, 168.5, 132.7, 130.3, 128.9, 128.0, 40.1, 31.8, 29.2, 29.1, 25.2, 22.8, 14.3; IR (thin film) cm$^{-1}$ 3263, 2927, 2857, 1717, 1682, 1650, 1576, 1557, 1537, 1451, 1420, 1349; MS m/z 279.9 [M+H]$^+$; calcd for C$_{15}$H$_{22}$NO$_2$S 280.1; overall yield: 67%.

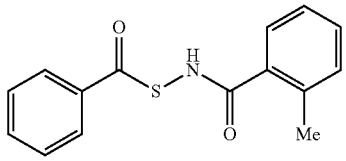

24

24 was prepared from thiobenzoic acid using the same procedure as 2. 2-Methylbenzoic anhydride was used in step 2. m.p. 106-108° C.; $^1$H NMR (300 MHz, CDCl$_3$) δ 7.93 (d, J=7.5 Hz, 2H), 7.65 (t, J=7.5 Hz, 2H), 7.51 (t, J=7.8 Hz, 2H), 7.39 (t, J=8.4 Hz, 1H), 7.28 (t, J=7.8 Hz, 2H), 6.68 (s, 1H), 2.54 (s, 3H); $^{13}$C NMR (75 MHz, CDCl$_3$) δ 191.3, 171.2, 137.3, 134.6, 133.0, 132.1, 131.4, 131.0, 129.3, 127.5; IR (thin film) cm$^{-1}$ 3262, 1697, 1670, 1576, 1557, 1541, 1420, 1208, 902; MS m/z 272.0 [M+H]$^+$; calcd for C$_{15}$H$_{14}$NO$_2$S 272.1; overall yield: 70%.

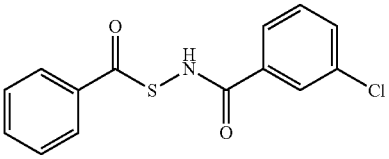

25

25 was prepared from thiobenzoic acid using the same procedure as 2. 3-Chlorobenzoic anhydride was used in step 2. m.p. 96-98° C.; $^1$H NMR (300 MHz, CDCl$_3$) δ 8.08 (t, J=1.8 Hz, 1H), 7.99 (dt, J=7.8, 1.2 Hz, 1H), 7.81 (dt, J=7.8, 1.2 Hz, 1H), 7.65 (tt, J=7.5, 1.2 Hz, 3H), 7.43 (dd, J=7.8, 2.4 Hz, 2H), 7.13 (s, 1H); $^{13}$C NMR (75 MHz, CDCl$_3$) δ 194.7, 170.4, 134.7, 134.0, 132.8, 130.4, 130.1, 129.3, 128.5, 128.4, 127.3, 126.1; IR (thin film) cm$^{-1}$ 3246, 1699, 1573, 1438, 1307, 1253, 1208, 900, 748; MS m/z 291.9 [M+H]$^+$; calcd for C$_{14}$H$_{11}$ClNO$_2$S 292.0; overall yield: 73%.

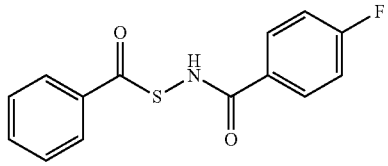

26

26 was prepared from thiobenzoic acid using the same procedure as 2. 4-Fluorobenzoic anhydride was used in step 2. m.p. 111-114° C.; $^1$H NMR (300 MHz, CDCl$_3$) δ 7.92 (m, 41-1), 7.64 (t, J=7.5 Hz, 1H), 7.48 (t, J=8.1 Hz, 2H), 7.34 (s, 1H), 7.11 (t, J=8.7 Hz, 2H); $^{13}$C NMR (75 MHz, CDCl$_3$) δ 191.1, 167.2, 134.7, 134.3, 130.6, 130.5, 129.3, 127.3, 116.3, 116.0; IR (thin film) cm$^{-1}$ 3357, 1654, 1561, 1541, 1498, 1439, 1420, 1236, 1209, 1158, 904; MS m/z 276.0 [M+H]$^+$; calcd for C$_{14}$H$_{11}$FNO$_2$S 276.0; overall yield: 66%.

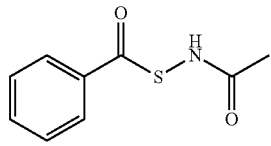

27

27 was prepared from thiobenzoic acid using the same procedure as 2. Acetic anhydride was used in step 2. m.p. 114-115° C.; $^1$H NMR (300 MHz, CDCl$_3$) δ 7.87 (d, J=7.2 Hz, 2H), 7.61 (t, J=6.9 Hz, 1H), 7.47 (t, J=7.5 Hz, 2H), 6.73 (s, 1H), 2.30 (s, 3H); $^{13}$C NMR (75 MHz, CDCl$_3$) δ 192.3, 166.1, 148.3, 134.6, 129.2, 127.3, 23.6; IR (thin film) cm$^{-1}$ 3279, 1701, 1682, 1670, 1556, 1537, 1208, 900; MS m/z 413.2 [2M+Na]$^+$; calcd for C$_{18}$H$_{18}$N$_2$NaO$_4$S$_2$ 413.0; overall yield: 75%.

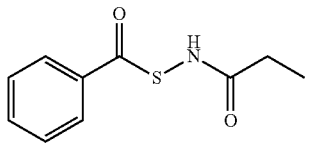

28

28 was prepared from thiobenzoic acid using the same procedure as 2. Propionic anhydride was used in step 2. m.p. 132-133° C.; $^1$H NMR (300 MHz, CDCl$_3$) δ 7.87 (d, J=8.7 Hz, 2H), 7.62 (t, J=7.2 Hz, 1H), 7.47 (t, J=7.5 Hz, 2H), 6.56 (s, 1H), 2.53 (q, J=7.5 Hz, 2H), 1.27 (t, J=7.2 Hz, 3H); $^{13}$C NMR (75 MHz, CDCl$_3$) δ 192.9, 175.4, 134.5, 129.2, 127.3, 30.1, 10.0; IR (thin film) cm$^{-1}$ 3221, 1699, 1670, 1557, 1537, 1458, 1416, 1208, 1173, 904; MS m/z 232.1 [M+Na]$^+$; calcd for C$_{10}$H$_{11}$NNaO$_2$S 232.0; overall yield: 72%.

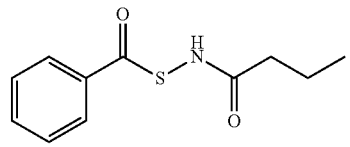

29

29 was prepared from thiobenzoic acid using the same procedure as 2. Butyric anhydride was used in step 2. m.p. 77-78° C.; NMR (300 MHz, CDCl$_3$) δ 7.82 (d, J=8.1 Hz, 2H), 7.56 (t, J=7.5 Hz, 1H), 7.42 (t, J=7.5 Hz, 2H), 6.31 (s, 1H), 2.42 (t, J=6.9 Hz, 2H), 1.74 (q, J=6.9 Hz, 2H), 0.97 (t, J=7.5 Hz, 3H); $^{13}$C NMR (75 MHz, CDCl$_3$) δ 192.5, 168.9, 134.5, 129.2, 127.3, 127.2, 38.9, 19.4, 13.9; IR (thin film) cm$^{-1}$ 3349, 2927, 1701, 1685, 1670, 1654, 1560, 1540, 1457, 1420, 1212; MS m/z 223.9 [M+H]$^+$; calcd for C$_{11}$H$_{14}$NO$_2$S 224.1; overall yield: 76%.

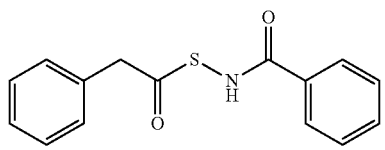

30

30 was prepared from 2-phenylethanethioic S-acid using the same procedure as 2. m.p. 96-98° C.; $^1$H NMR (300 MHz, CDCl$_3$) δ 7.82 (d, J=7.2 Hz, 2H), 7.75 (s, 1H), 7.48 (t, J=7.2 Hz, 1H), 7.36 (d, J=7.8 Hz, 2H), 7.28 (m, 5H), 3.76 (s, 2H); $^{13}$C NMR (75 MHz, CDCl$_3$) δ 197.5, 168.7, 132.9, 132.7, 132.0, 130.1, 129.1, 128.9, 128.1, 128.0; IR (thin film) cm$^{-1}$ 3292, 1705, 1662, 1556, 1541, 1451, 1416, 1353, 1158, 989; MS m/z 272.0 [M+H]$^+$; calcd for C$_{15}$H$_{14}$NO$_2$S 272.1; overall yield: 54%.

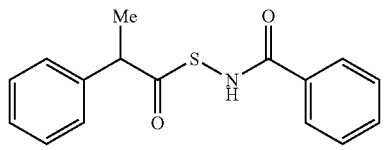

31

31 was prepared from 2-phenylpropanethioic S-acid using the same procedure as 2. m.p. 121-122° C.; $^1$H NMR (300 MHz, CDCl$_3$) δ 7.82 (d, J=7.2 Hz, 2H), 7.54 (t, J=7.2 Hz, 1H), 7.44 (t, J=7.8 Hz, 2H), 7.36 (s, 5H), 6.91 (s, 1H), 3.92 (q, J=7.2 Hz, 1H), 1.60 (d, J=7.2 Hz, 3H); $^{13}$C NMR (75 MHz, CDCl$_3$) δ 200.6, 165.8, 138.1, 133.2, 132.7, 129.2, 129.0, 128.6, 128.4, 127.8, 51.2, 18.1; IR (thin film) cm$^{-1}$ 3420, 1700, 1661, 1499, 1453, 1423, 1264, 947; MS m/z 286.0 [M+H]$^+$; calcd for C$_{16}$H$_{16}$NO$_2$S 286.1; overall yield: 55%.

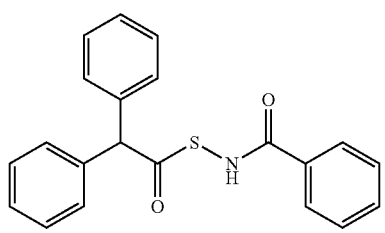

32

32 was prepared from 2,2-diphenylethanethioic S-acid using the same procedure as 2. m.p. 144-145° C.; $^1$H NMR (300 MHz, CDCl$_3$) δ 7.83 (d, J=7.8 Hz, 2H), 7.54 (t, J=6.9 Hz, 1H), 7.43 (t, J=7.5 Hz, 2H), 7.34 (m, 10H), 7.06 (s, 1H), 5.19 (s, 1H); $^{13}$C NMR (75 MHz, CDCl$_3$) δ 198.9, 163.1, 137.1, 133.1, 132.7, 129.4, 129.1, 129.0, 128.2, 127.9, 61.8; IR (thin film) cm$^{-1}$ 3284, 1707, 1662, 1560, 1537, 1494, 1452, 1423, 1849, 992; MS m/z 348.1 [M+H]$^+$; calcd for C$_{21}$H$_{18}$NO$_2$S 348.1; overall yield: 59%

Scheme 6: Synthetic route to compound 33

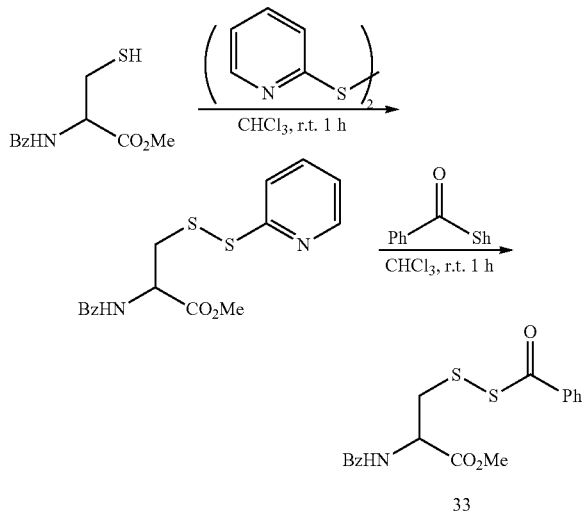

To a stirred solution of N-benzoyl cysteine methyl ester (120 mg, 0.5 mmol) in CHCl$_3$ (8 mL) was added 2-mercapto pyridine disulfide (220 mg, 1 mmol). The solution was stirred for 1 hour at room temperature. The asymmetric disulfide compound was isolated by column chromatography (hexane: ethyl acetate=2H). To this disulfide compound in CHCl$_3$ (5 mL) was then added thiobenzoic acid (138 mg, 1 mmol) and the solution was stirred for 1 hour at room temperature. The product 33 was obtained by column chromatography (hexane:ethyl acetate=10:4) as white solid (overall yield: 68%). m.p. 94-96° C.; $^1$H NMR (300 MHz, CDCl$_3$) δ 7.97 (d, J=6.9 Hz, 2H), 7.90 (d, J=7.8 Hz, 2H), 7.80 (d, J=7.5 Hz, 1H), 7.61 (t, J=7.5 Hz, 1H), 7.47 (m, 5H), 5.06 (m, 1H), 3.70 (s, 3H), 3.57 (dd, J=14.4, 4.8 Hz, 1H) 3.30 (dd, J=14.4, 4.8 Hz, 1H); $^{13}$C NMR (75 MHz, CDCl$_3$) δ 191.3, 170.8, 167.3, 135.3, 134.7, 133.7, 132.1, 129.2, 128.8, 128.0, 127.6, 53.0, 51.8, 40.9; IR (thin film) cm$^{-1}$ 3357, 3060, 2950, 1744, 1717, 1682, 1646, 1576, 1556, 1541, 1517, 1486, 1337, 1205, 1173; MS m/z 398.1 [M+Na]$^+$; calcd for C$_{18}$H$_{17}$NNaO$_4$S$_2$ 398.0.

Scheme 7: Synthetic route to compound 34

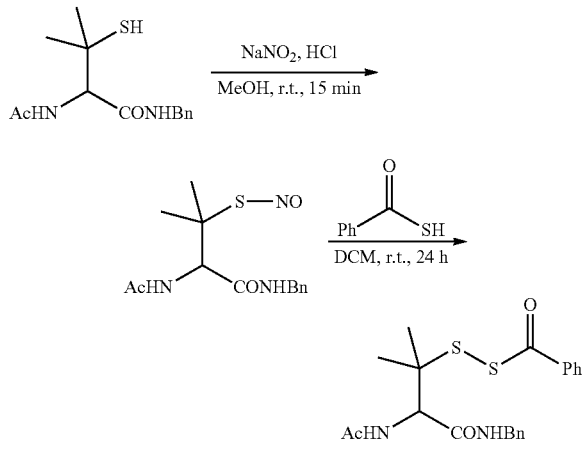

The thiol starting material (112 mg, 0.4 mmol) was dissolved into 20 mL MeOH, followed by the addition of NaNO$_2$ (138 mg, 2 mmol) and HCl (2.0 mL, 1.0 M). The solution was stirred at room temperature for 15 minutes. Then the mixture was extracted 3 times with brine and CH$_2$Cl$_2$. Organic layers were combined, dried over MgSO$_4$ and removed under reduced pressure to provide the S-nitrosated product. This intermediate was then dissolved into 15 mL CH$_2$Cl$_2$ containing thiobenzoic acid (138 mg, 1 mmol). The resultant solution was stirred at room temperature for 24 hours and washed with saturated NaHCO$_3$ aqueous solution (3 times). The organic solvent was then concentrated and the crude product was purified by column chromatography (1% MeOH in CH$_2$Cl$_2$) to furnish compound 34. Overall yield: 30%. m.p. 143-145° C.; $^1$H NMR (300 MHz, CDCl$_3$) δ 8.55 (m, 1H), 8.00 (d, J=7.5 Hz, 2H), 7.63 (t, J=7.5 Hz, 1H), 7.48 (t, J=7.8 Hz, 2H), 7.32 (m, 5H), 7.15 (d, J=7.8 Hz, 1H), 4.57 (d, J=7.8 Hz, 1H), 4.47 (dd, J=15.0, 5.4 Hz, 1H), 2.00 (s, 3H), 1.88 (s, 3H), 1.48 (s, 3H), 1.24 (s, 3H); $^{13}$C NMR (75 MHz, CDCl$_3$) δ 193.8, 170.5, 169.1, 138.2, 135.5, 134.8, 129.2, 128.8, 128.3, 128.0, 127.6, 58.8, 53.9, 44.0, 26.9, 24.2, 23.4; IR (thin film) cm$^{-1}$ 3314, 2360, 1765, 1658, 1641, 1631, 1598, 1443, 1382, 1202; MS m/z 439.1 [M+Na]$^+$; calcd for C$_{21}$H$_{24}$N$_2$NaO$_3$S$_2$ 439.1.

Example 2

Methylene Blue Experiment for H$_2$S Release in PBS Buffer

Na$_2$S Standard Curve for H$_2$S Release 2.0 mM Na$_2$S stock solution was prepared as described in previous section. Five aliquots of Na$_2$S solution at 3.75 µL, 7.50 µL, 15.0 µL, 45.0 µL, and 112.5 µl were injected into the 4-mL vials containing H$_2$O (1.0 mL), zinc acetate (1% w/v, 100 µL), N,N-dimethyl-1,4-phenylenediamine sulfate (200 µL, 20 mM) in 7.2 M HCl and ferric chloride (200 µL, 30 mM) in 1.2 M HCl, respectively. Stir the resultant solution for 15 minutes at room temperature. The absorbance (670 nm) of aliquots was determined using a UV-Vis spectrometer.

H$_2$S Release in PBS Buffer

Cysteine stock solution in H$_2$O (400 mM, 112.5 µL) and N-(benzoylthio)benzamide 2 stock solution in THF (40 mM, 112.5 µL) were added into PBS buffer solution (30 mL, pH=7.4) containing EDTA (50 mM, 60 µL), respectively. Every 3 minute, 1.0 mL of aliquots were taken to 4-mL vials containing, zinc acetate (1% w/v, 100 µL), N,N-dimethyl-1, 4-phenylenediamine sulfate (200 µL, 20 mM) in 7.2 M HCl and ferric chloride (200 µL, 30 mM) in 1.2 M HCl within 3 hours. Then the absorbance (670 nm) was determined using a UV-Vis spectrometer.

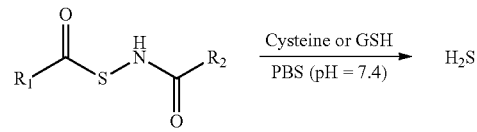

The initial concentrations of H$_2$S-donors shown below were 150 µM and the detection of H$_2$S released from these molecules was measured in presence of 1.5 mM of cysteine or GSH, unless otherwise indicated.

TABLE 1
| | H₂S generation parameters of donors | | | |
| --- | --- | --- | --- | --- |
| | Cys | | GSH | |
| Donors | Peaking time (min) | [H₂S] at peaking time (μM) | Peaking time (min) | [H₂S] at peaking time (μM) |
| 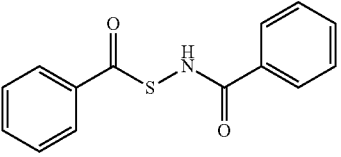 2 | 24 | 143.6 | 39 | 140.4 |
| 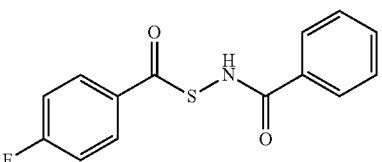 3 | 18 | 143.1 | 36 | 122.6 |
| 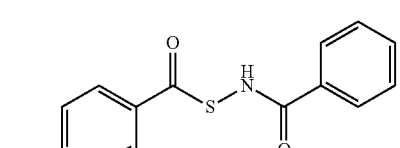 4 | 26 | 110.0 | 27 | 59.5 |
| 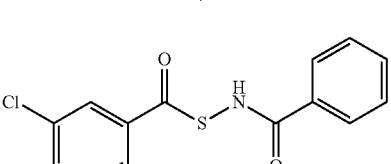 5 | 24 | 142.1 | 36 | 146.5 |
| 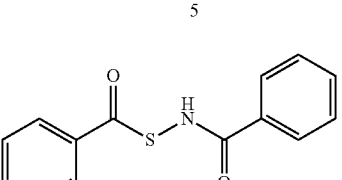 6 | 34 | 85.0 | 45 | 61.9 |
| 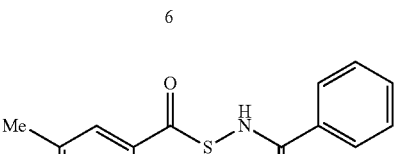 7 | 28 | 141.8 | 39 | 131.0 |
| 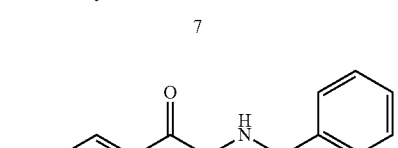 8 | 27 | 93.9 | 30 | 100.3 |

TABLE 1-continued

H₂S generation parameters of donors

| Donors | Cys | | GSH | |
|---|---|---|---|---|
| | Peaking time (min) | [H₂S] at peaking time (μM) | Peaking time (min) | [H₂S] at peaking time (μM) |
| 9 | 36 | 52.8 | 48 | 48.3 |
| 10 | 25 | 111.6 | 20 | 133.6 |
| 11 | 27 | 92.4 | 40 | 100.5 |
| 12 | 50 [a] | 23.0 [a] | 120 [a] | 13.2 [a] |
| 13 | 22 [a] | 17.5 [a] | 30 [a] | 15.0 [a] |
| 14 | 15 | 33.9 | 30 | 23.4 |
| 16 | 18 | 72.4 | 36 | 81.9 |

TABLE 1-continued
H₂S generation parameters of donors
| Donors | Cys | | GSH | |
|---|---|---|---|---|
| | Peaking time (min) | [H₂S] at peaking time (μM) | Peaking time (min) | [H₂S] at peaking time (μM) |
| 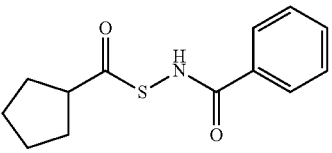 17 | 18 | 100.6 | 32 | 110.9 |
| 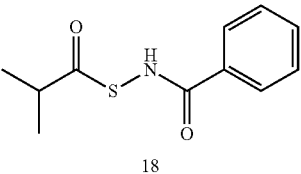 18 | 36 | 131.6 | 52 | 101.1 |
| 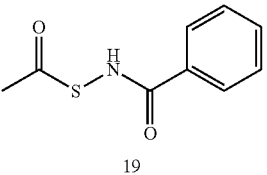 19 | 12 | 132.6 | 18 | 116.1 |
| 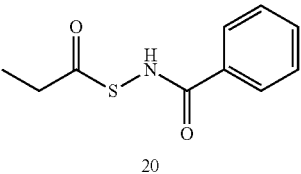 20 | 28 | 106.1 | 35 | 103.6 |
| 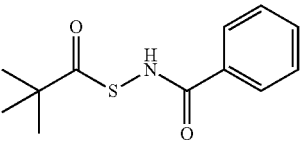 21 | 55 | 106.4 | 90 | 96.6 |
| 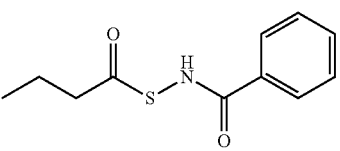 22 | 39 | 111.3 | 40 | 122.3 |
| 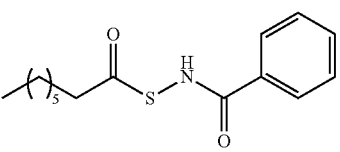 23 | 50 | 125.1 | 65 | 111.4 |

TABLE 1-continued
| | H₂S generation parameters of donors | | | |
|---|---|---|---|---|
| | Cys | | GSH | |
| Donors | Peaking time (min) | [H₂S] at peaking time (μM) | Peaking time (min) | [H₂S] at peaking time (μM) |
| 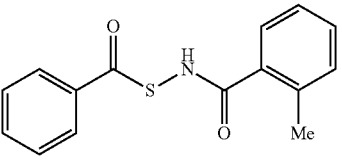 24 | 24 | 146.9 | 30 | 130.5 |
| 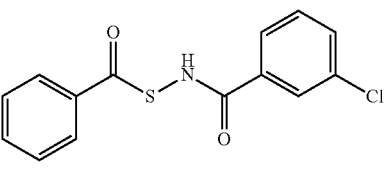 25 | 26 | 83.6 | 27 | 84.3 |
| 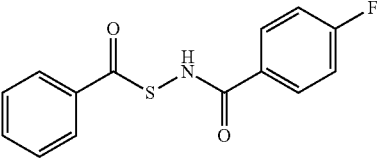 26 | 34 | 110.6 | 42 | 104.1 |
| 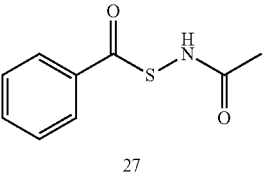 27 | 30 | 145.4 | 39 | 149.6 |
| 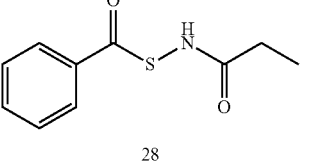 28 | 34 | 120.9 | 50 | 116.6 |
| 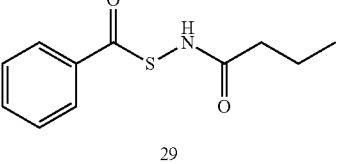 29 | 30 | 102.8 | 39 | 98.9 |
| 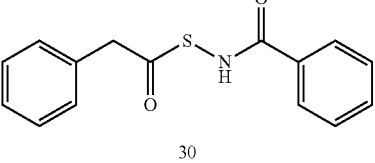 30 | 30 | 108.6 | 44 | 104.9 |

TABLE 1-continued

H₂S generation parameters of donors

| Donors | Cys | | GSH | |
|---|---|---|---|---|
| | Peaking time (min) | [H$_2$S] at peaking time (μM) | Peaking time (min) | [H$_2$S] at peaking time (μM) |
| 31 (PhCH(Me)C(O)–S–NHC(O)Ph) | 36 | 130.4 | 52 | 103.8 |
| 32 (Ph$_2$CHC(O)–S–NHC(O)Ph) | 60 | 45.6 | N/A [b] | N/A [b] |
| 33 (BzHN–CH(CO$_2$Me)–CH$_2$–S–S–C(O)Ph) | 35 | 25.8 | 45 | 18.3 |
| 34 (AcHN–C(Me)$_2$(CONHBn)–... –S–S–C(O)Ph) | 33 | 149 | 39 | 137 |

[a] The concentrations of donors were 40 μM and cysteine was 4.0 mM.
[b] H$_2$S generation was not observed within the experimental period of 3 hours.

Example 3

H$_2$S Release Measurement in Plasma

Figure 2:
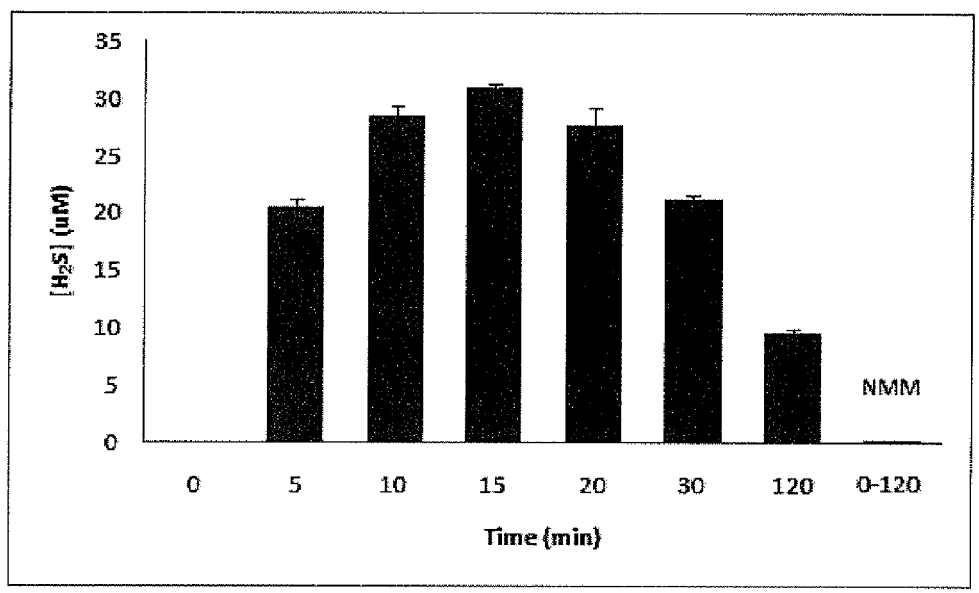
FIG. 2: $H_2S$ generation from 2 in plasma.

It is known that plasma contains significant amount of free cysteine. We therefore measured H$_2$S generation of 2-13 in plasma (containing ~500 μM cysteine) using a colorimetry method. We observed a similar time-dependent H$_2$S release (FIG. 2, illustrated an example using 2) as the one shown in FIG. 1. However, when plasma was first treated with N-methylmaleimide (NMM) to block free cysteine, no H$_2$S generation was observed. These results demonstrated the capability of H$_2$S release from N-(benzoylthio)benzamide-based donors in complex biological systems. It is also demonstrated that cysteine is the regulator of this type of donors.

Calibration Curve in Plasma

To 0.5 mL of bovine/calf plasma was added 0.5 mL water solution containing zinc acetate (1% w/v, 100 μL) and trichloroacetic acid (10% w/v, 600 μL). The mixture was allowed to centrifuge for 10 min (5000 g). The precipitate was filtered out and 1.2 mL of the clear solution was transferred into a 2-mL vial containing N,N-dimethyl-1,4-phenylenediamine sulfate (150 μL, 20 mM) in 7.2 M HCl and ferric chloride (150 μL, 30 mM) in 1.2 M HCl. To five of these aliquots were added 10 μL, 20 μL, 25 μL, 30 μL, 40 μL methylene blue (MB$^+$) stock solution in H$_2$O (1 mM), respectively. The absorbance (670 nm) of aliquots of the resulting solution (1.5 mL) was determined using a UV-VIS spectrometer. The concentration of MB$^+$ was then converted to the concentration of H$_2$S according to the reaction equation shown above and the calibration curve was generated by plotting the absorbance versus [H$_2$S].

H$_2$S Release in Plasma

To 2.0 mL of bovine/calf plasma (containing cysteine ~2 μmol) was added 2 mL water solution containing 5a (25 μl, of 80 mM in DMSO). The solution was stirred at room temperature. Reaction aliquots (1 mL) were collected into 2-mL vials containing zinc acetate (1% w/v, 100 μL) and trichloroacetic acid (10% w/v, 600 μL) in every 5 minutes. The resulting mixture was centrifuged for 10 minutes (5000 g) and the precipitate was filtered. The clear solution (1.2 mL) was transferred to another 2-mL vial. Subsequently, N,N-dimethyl-p-phenylenediamine sulfate (20 mM, 150 μL) in 7.2 M HCl was added followed by FeCl₃ (30 mM, 150 μL) in 1.2 M HCl, and absorbance (670 nm) of aliquots of the resulting solution (1.5 mL) was determined 20 minutes thereafter using a UV-Vis spectrometer.

Example 4

Perthiol $H_2S$ Donors

Perthiol $H_2S$ donors are also provided by the invention. In one embodiment, the perthiol donors are cysteine based; in a second embodiment, they are penicillamine based.

Cysteine Based Perthiol $H_2S$ Donors

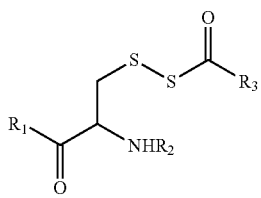

$R_1$ = OH, OR' (R' = alkyl), NHBn, etc.
$R_2$ = acyl, alkyl, etc.
$R_3$ = alkyl, aryl, etc.

examples:

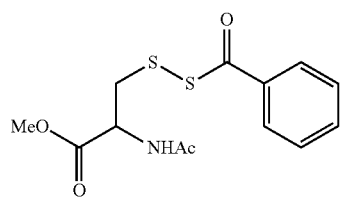

E1

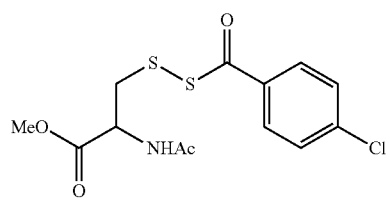

E2

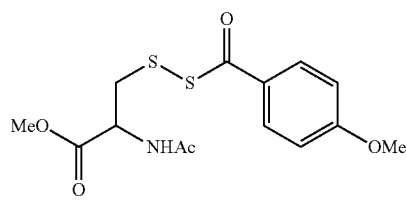

E3

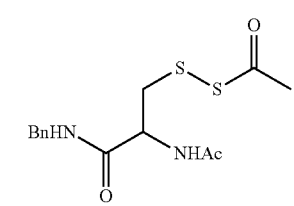

E4

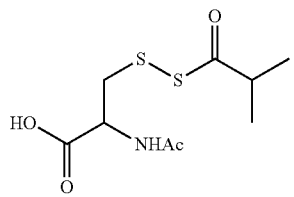

E5

Typical synthesis (using E3 as the example):

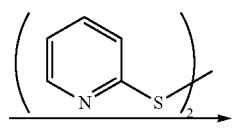

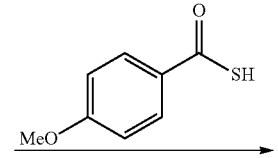

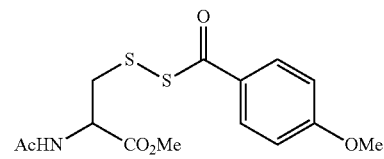

Protected cysteine starting materials are converted to 2-mercapto pyridine disulfide intermediates. The reactive disulfide intermediates are then treated with corresponding thiocarboxylic acids to afford the $H_2S$ donors.

Penicillamine Based Perthiol $H_2S$ Donors

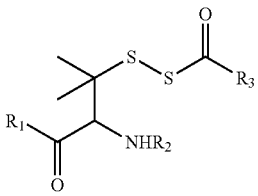

$R_1$ = OH, OR' (R' = alkyl), NHBn, etc.
$R_2$ = acyl, alkyl, etc.
$R_3$ = alkyl, aryl etc.

examples:

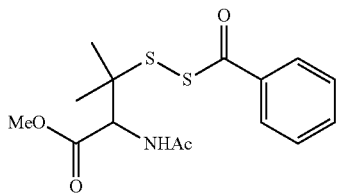

E6

-continued

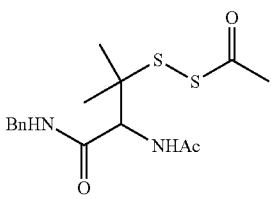

E7

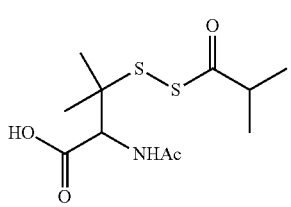

E8

Typical synthesis:

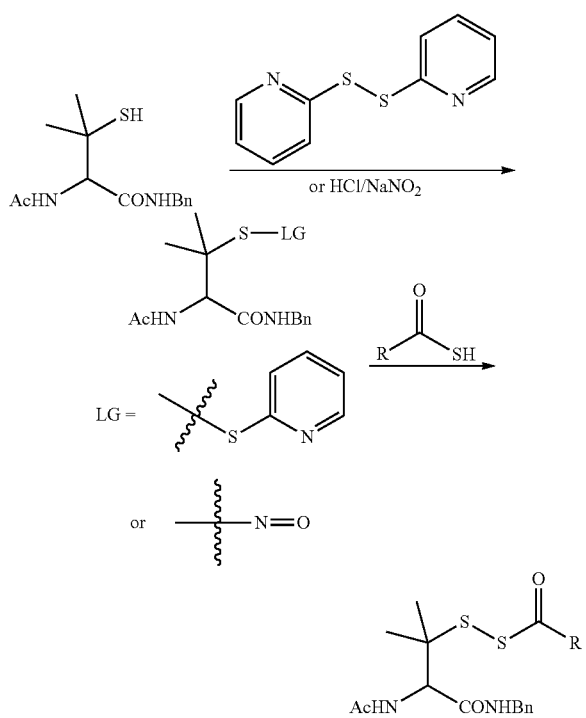

Protected penicillamine starting materials are converted to S-activated intermediates with a leaving group (LG) on the sulfur atom. The leaving group is, for example, 2-mercapto pyridine or a nitroso group. The synthesis of these two intermediates is achieved by reacting the starting materials with 2-mercapto pyridine disulfide or NaNO$_2$ in acidic conditions, respectively. The resultant intermediates are treated with different thiocarboxylic acids to produce the desired H$_2$S donors.

Example 5

Biological Activity

The effects of compound 2 have been tested using the mouse model of Elrod et al. (*Proc. Natl. Acad. Sci. USA* 2007, 104, 15560). Briefly, mice were subjected to ischemia followed by reperfusion. During reperfusion, compound 2 was administered to the mice. Compared to vehicle treated mice, mice receiving 2 displayed a dose-dependent reduction in infarct size per area-at-risk (INF/AAR), with a 100 μg/kg bolus of 2 maximally reducing INF/AAR by 40%.

These results suggest that administration of the H$_2$S generating compounds of the invention substantially decreases the size of myocardial infarction that occurs as the result of ischemia and reperfusion, in living animals.

REFERENCES

Calvert, J. W.; Coetzee, W. A.; Lefer, D. J. Antioxid. Redox Signal. 2010, 12, 1203.
Gadalla, M. M.; Snyder, S. H. J. Neurochem. 2010, 113, 14.
Kabil, O.; Banerjee, R. J. Biol. Chem. 2010, 285, 21903.
Szabo, C. Nat. Rev. 2007, 6, 917.
Lowicka, E.; Beltowski, J. Pharmaco. Rep. 2007, 59, 4.
Blackstone, E.; Morrison, M.; Roth, M. B. Science 2005, 308, 518.
Caliendo, G.; Cirino, G.; Santagada, V.; Wallace, J. L. J. Med. Chem. 2010, 53, 6275.
Jacob, C.; Anwar, A.; Burkholz, T. Planta Medica. 2008, 74, 1580.
Benavides, G. A.; Squadrito, G. L.; Mills, R. W.; Patel, H. D.; Isbell, T. S.; Patel, R. P.;
Darley-Usmar, V. M.; Doeller, J. E.; Kraus, D. W. Proc. Natl. Acad. Sci. USA 2007, 104, 17977.
Li, L.; Salto-Tellex, M.; Tang, C. H.; Whiteman, M.; Moore, P. K. Free Radic. Biol. Med. 2009, 47, 103.
Li, L.; Whiteman, M.; Guan, Y. Y.; Neo, K. L.; Cheng, Y.; Lee, S. W.; Zhao, Y.; Baskar, R.; Tan, C. H.; Moore, P. L. Circulation 2008, 117, 2351.
Baskar, R.; Sparatore, N.; Del Soldato, P.; Moore, P. K. Eur. J. Pharm. 2008, 594, 1
Morra, M. J.; Dick, W. A. Appl. Envir. Microbiol. 1991, 57, 1413.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

We claim:
1. An agent for the controlled, sustained release of H$_2$S having the chemical formula

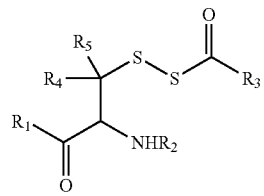

where R1, R2 and R3 vary independently and: R1 is selected from the group consisting of OH, OR', NHR', and NR'R" where R' and R' are selected from the group consisting of alkyl, aryl, and heteroaryl, R2 is selected from the group consisting of acyl, alkyl, aryl, and sulfonyl, R3 is selected from the group consisting of alkyl, aryl, substituted aryl, and heteroaryl, and R4 and R5 are independently selected from the group consisting of H, methyl or alkyl, substituted alkyl, aryl, and substituted aryl.

2. The agent of claim 1, wherein said agent has the chemical formula
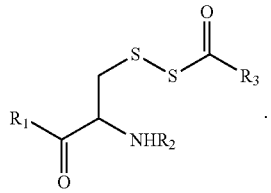
Formula 5
3. The agent of claim 1, wherein said agent has the chemical formula
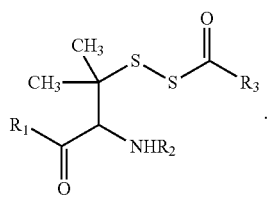
Formula 6
\* \* \* \* \*